(12) United States Patent
Appenzeller et al.

(10) Patent No.: US 8,080,061 B2
(45) Date of Patent: Dec. 20, 2011

(54) APPARATUS AND METHODS FOR TREATING BONE

(75) Inventors: Andreas Appenzeller, Biel (CH); Christof Dutoit, Solothurn (CH); Alfred Benoit, Lengnau (CH); Thierry Stoll, Meinisberg (CH); Erich Röthlisberger, Biel (CH); Stefan Mathys, Basel (CH)

(73) Assignee: Synthes USA, LLC, West Chester, PA (US)

(*) Notice: Subject to any disclaimer, the term of this patent is extended or adjusted under 35 U.S.C. 154(b) by 822 days.

(21) Appl. No.: 11/471,169

(22) Filed: Jun. 19, 2006

(65) Prior Publication Data
US 2007/0055274 A1    Mar. 8, 2007

Related U.S. Application Data

(60) Provisional application No. 60/692,408, filed on Jun. 20, 2005, provisional application No. 60/715,188, filed on Sep. 8, 2005, provisional application No. 60/722,064, filed on Sep. 28, 2005, provisional application No. 60/725,773, filed on Oct. 12, 2005, provisional application No. 60/726,835, filed on Oct. 13, 2005, provisional application No. 60/728,442, filed on Oct. 19, 2005, provisional application No. 60/730,909, filed on Oct. 27, 2005, provisional application No. 60/733,026, filed on Nov. 3, 2005, provisional application No. 60/733,647, filed on Nov. 4, 2005, provisional application No. 60/753,782, filed on Dec. 23, 2005.

(51) Int. Cl.
*A61F 2/44* (2006.01)
*A61B 17/58* (2006.01)

(52) U.S. Cl. .......... 623/17.11; 623/17.16; 606/86 R; 606/90; 606/99

(58) Field of Classification Search .......... 606/246, 606/249, 62, 63, 86 R, 90, 99, 105; 623/17.11, 623/17.16; *A61B 17/56, 17/88; A61F 2/44, A61F 2/46*
See application file for complete search history.

(56) References Cited

U.S. PATENT DOCUMENTS
4,611,581 A    9/1986    Steffee
(Continued)

FOREIGN PATENT DOCUMENTS
EP    1308134    7/2003
(Continued)

OTHER PUBLICATIONS

Fürderer et al., "Vertebral body stenting," Orthopäde 31:356-361 (2002) (in German, with English language translation).
(Continued)

*Primary Examiner* — Thomas C. Barrett
*Assistant Examiner* — Michael T Schaper
(74) *Attorney, Agent, or Firm* — McKeon, Meunier, Carlin & Curfman

(57) ABSTRACT

Implants and methods for bone treatment, preferably minimally invasive treatment, including repositioning of vertebrae may comprise insertion of a bobbin having a wire, string, thread or band, coiled around the bobbin. During coiling, the diameter of the bobbing/band complex may increase. Such increase in diameter can push against the inner side of the endplates of the vertebral body, and augment the vertebral body to its original height. The implant may also take the form of a coiled sleeve which when inserted into the vertebral body is uncoiled. The force of the uncoiling sleeve pushes against the inner side of the endplates of the vertebral body, restoring the vertebral body to its original height. The implant may also take the form of fibrous masses comprised of a thread or other relatively thin structure, for example a fiber or strand, of any biocompatible material having desired characteristics, for example a shape memory alloy, titanium, stainless steel, another metal or metal alloy, a ceramic, a composite or any combination thereof. The strand, thread or other fiber may be coiled, woven, matted, tangled or otherwise formed into a wool-like mass or body having a desired configuration. Expansion of the expandable member within the vertebral body or other bone may reposition the fractured bone to a desired height and augment the bone to maintain the desired height. A bone cement or other filler can be added to further treat and stabilize the vertebral body or other bone.

21 Claims, 30 Drawing Sheets

U.S. PATENT DOCUMENTS

| | | | | |
|---|---|---|---|---|
| 5,059,193 | A * | 10/1991 | Kuslich | 606/247 |
| 5,637,042 | A * | 6/1997 | Breese | 464/183 |
| 5,693,100 | A * | 12/1997 | Pisharodi | 623/17.16 |
| 5,697,977 | A * | 12/1997 | Pisharodi | 606/279 |
| 5,782,831 | A | 7/1998 | Sherman et al. | |
| 5,919,235 | A * | 7/1999 | Husson et al. | 623/17.16 |
| 5,976,186 | A * | 11/1999 | Bao et al. | 623/17.16 |
| 6,127,597 | A * | 10/2000 | Beyar et al. | 606/86 R |
| 6,162,231 | A * | 12/2000 | Mikus et al. | 606/108 |
| 6,235,043 | B1 | 5/2001 | Reiley et al. | |
| 6,248,110 | B1 | 6/2001 | Reiley et al. | |
| 6,423,083 | B2 | 7/2002 | Reiley et al. | |
| 6,488,710 | B2 * | 12/2002 | Besselink | 623/17.15 |
| 6,576,016 | B1 * | 6/2003 | Hochshuler et al. | 623/17.15 |
| 6,764,514 | B1 * | 7/2004 | Li et al. | 623/17.12 |
| 7,241,297 | B2 * | 7/2007 | Shaolian et al. | 606/80 |
| 7,442,210 | B2 * | 10/2008 | Segal et al. | 623/17.12 |
| 2001/0001129 | A1 * | 5/2001 | McKay et al. | 623/17.16 |
| 2002/0068974 | A1 | 6/2002 | Kuslich et al. | |
| 2003/0018390 | A1 * | 1/2003 | Husson | 623/17.16 |
| 2003/0088249 | A1 | 5/2003 | Furderer | |
| 2004/0049282 | A1 * | 3/2004 | Gjunter | 623/17.16 |
| 2004/0059418 | A1 * | 3/2004 | McKay et al. | 623/17.16 |
| 2004/0073308 | A1 | 4/2004 | Kuslich et al. | |
| 2004/0097930 | A1 * | 5/2004 | Justis et al. | 606/61 |
| 2004/0117019 | A1 * | 6/2004 | Trieu et al. | 623/17.11 |
| 2004/0210226 | A1 * | 10/2004 | Trieu | 606/72 |
| 2004/0225361 | A1 * | 11/2004 | Glenn et al. | 623/17.12 |
| 2004/0249463 | A1 * | 12/2004 | Bindseil et al. | 623/17.16 |
| 2005/0015148 | A1 * | 1/2005 | Jansen et al. | 623/17.11 |
| 2005/0090824 | A1 * | 4/2005 | Shluzas et al. | 606/61 |
| 2006/0089715 | A1 | 4/2006 | Truckai et al. | |
| 2006/0095138 | A1 | 5/2006 | Truckai et al. | |
| 2006/0100706 | A1 * | 5/2006 | Shadduck et al. | 623/17.11 |
| 2006/0106459 | A1 | 5/2006 | Truckai et al. | |
| 2006/0122625 | A1 | 6/2006 | Truckai et al. | |
| 2006/0149268 | A1 | 7/2006 | Truckai et al. | |
| 2006/0271061 | A1 * | 11/2006 | Beyar et al. | 606/105 |
| 2008/0065067 | A1 * | 3/2008 | Steinberg | 606/53 |

FOREIGN PATENT DOCUMENTS

| | | |
|---|---|---|
| WO | WO 2004/047689 | 6/2004 |
| WO | WO 2004/086934 | 10/2004 |
| WO | WO 2005/027734 | 3/2005 |

OTHER PUBLICATIONS

Gaitanis et al., "Balloon kyphoplasty for the treatment of pathological vertebral compression fractures," Eur Spine 14:250-260 (2005).

Jang, "Pulmonary embolism of polymethylmethacrylate after percutaneous vertebroplasty: a report of three cases," Spine 27(19):E416-E418 (2002).

Lieberman et al., "Initial outcome and efficacy of kyphoplasty in the treatment of painful osteoporotic vertebral compression fractures," Spine 26(14):1631-1638 (2001).

Magerl et al., "A comprehensive classification of thoracic and lumbar injuries," Eur Spine 184-201 (1994).

Truumees, "Comparing kyphoplasty and vertebroplasty," Advances in Osteoporotic Fracture Management 1(4) (2002).

* cited by examiner

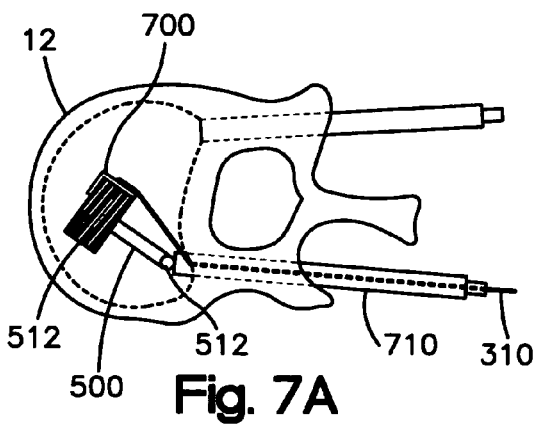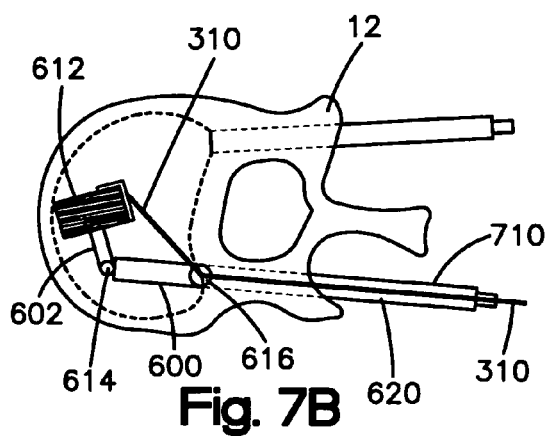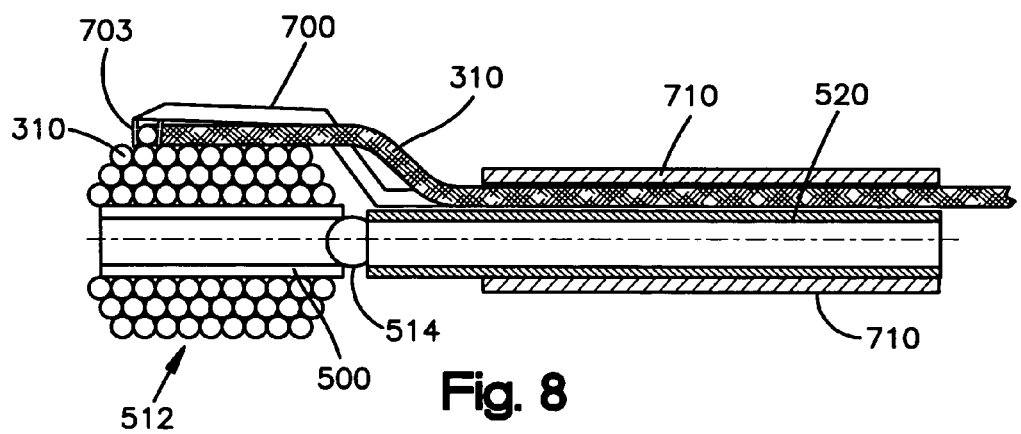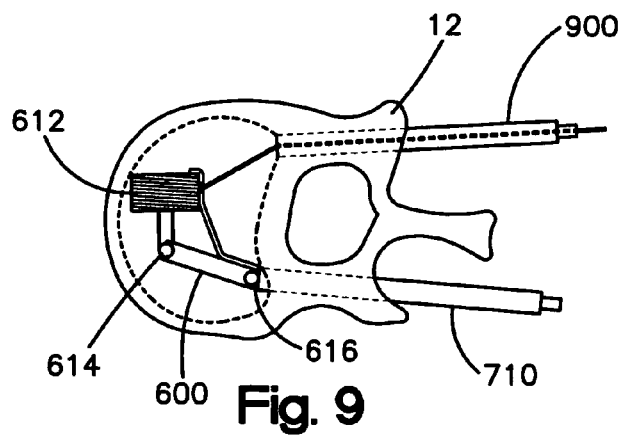

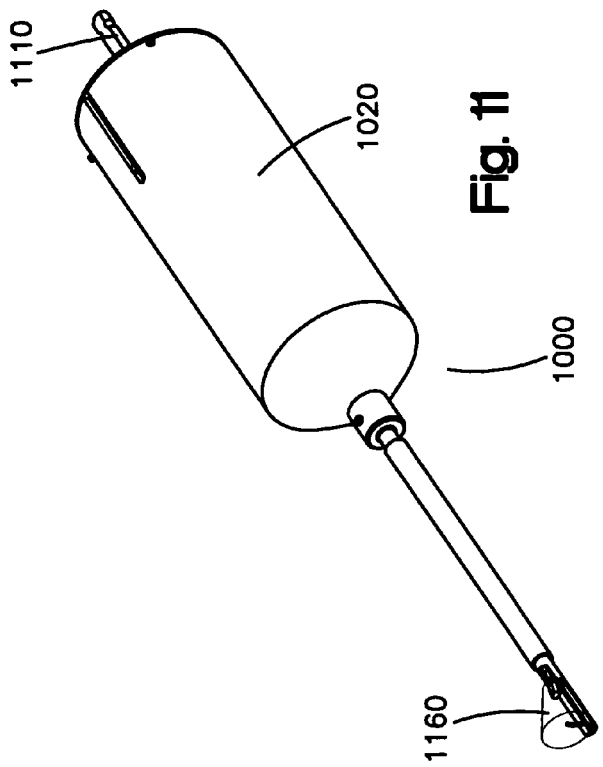
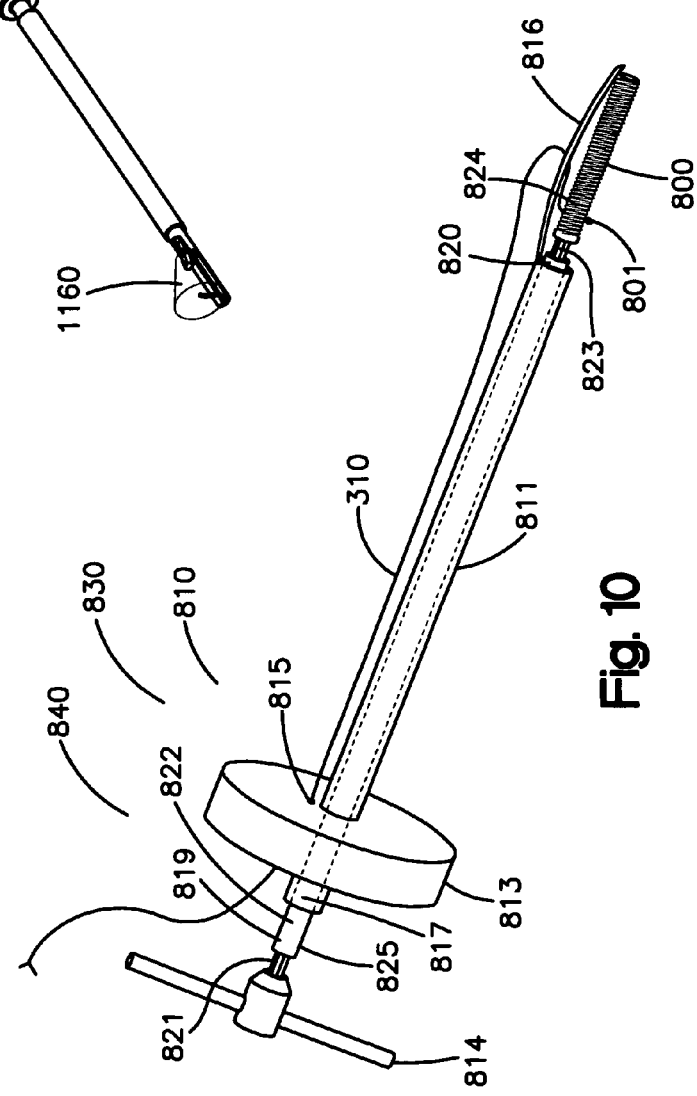

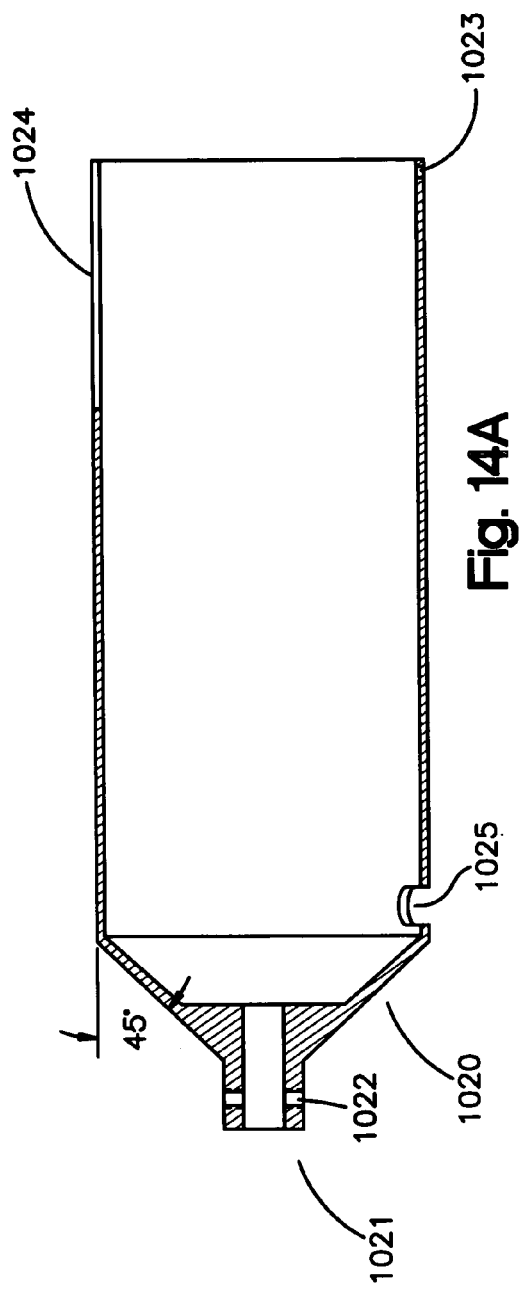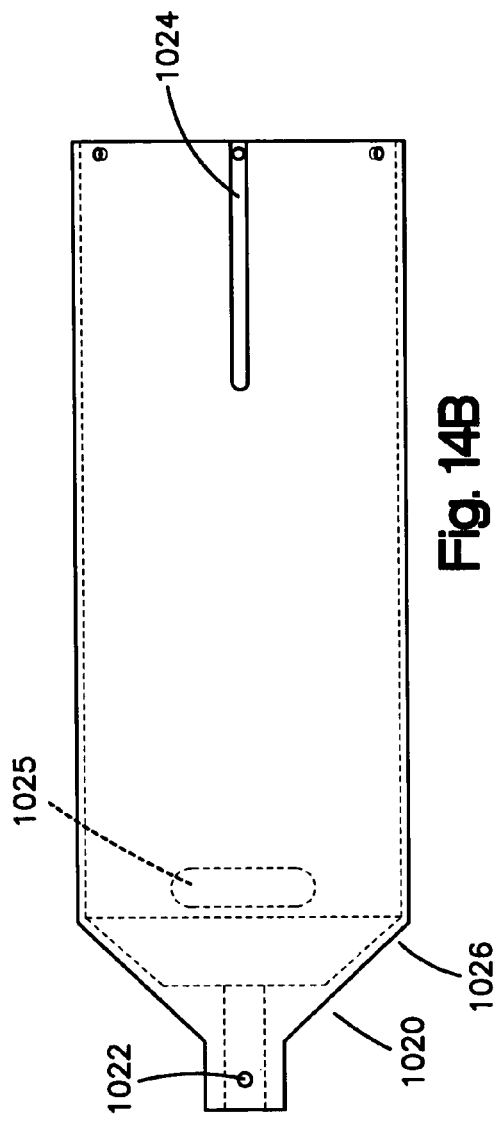

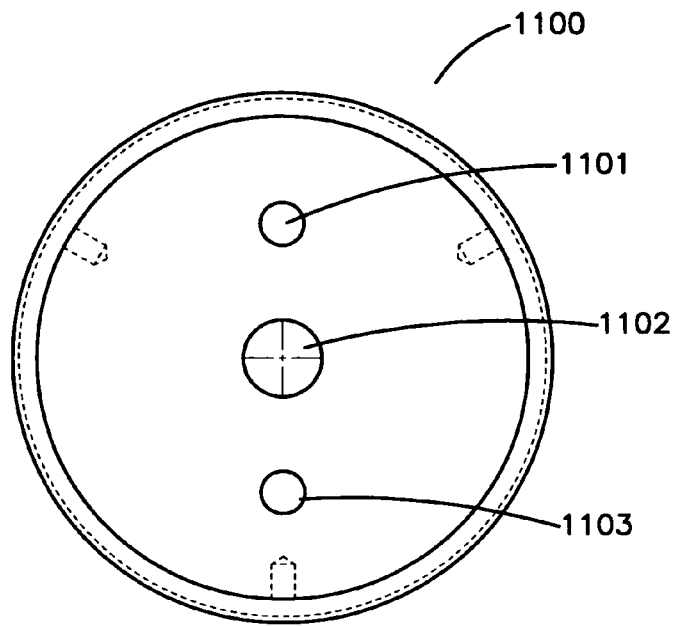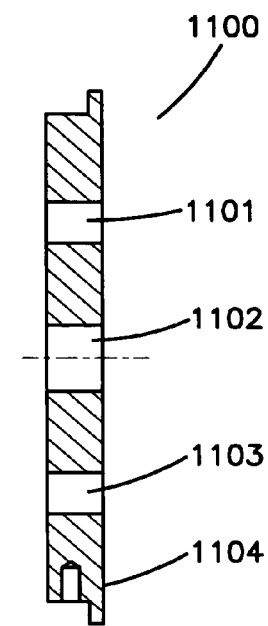
Fig. 15A            Fig. 15B
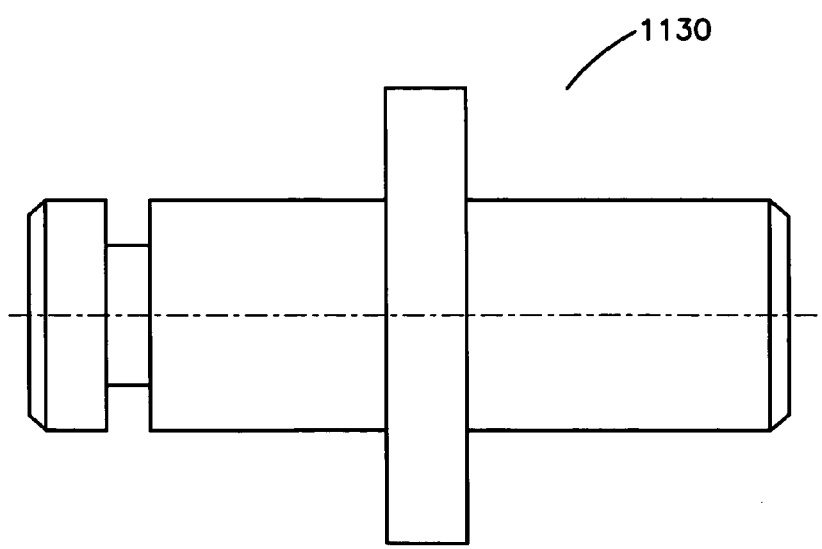
Fig. 16

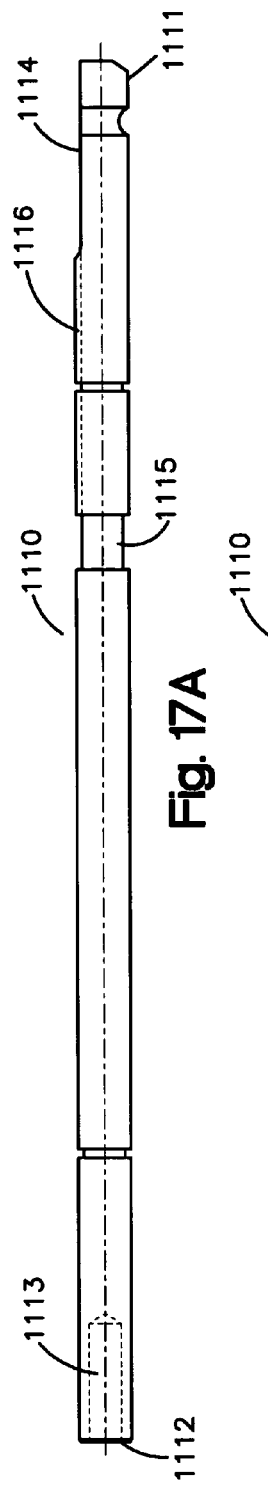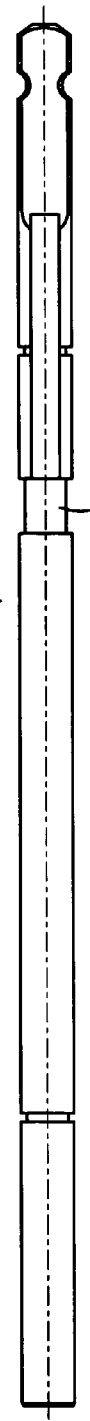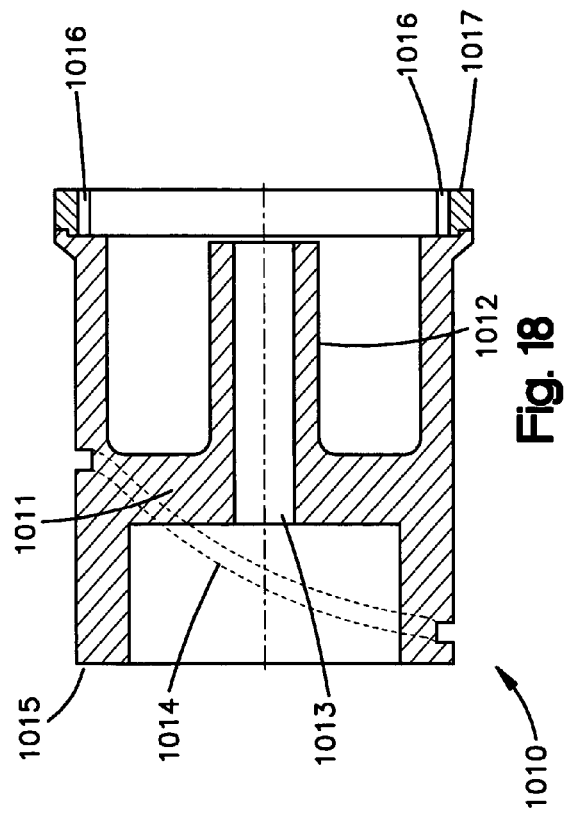

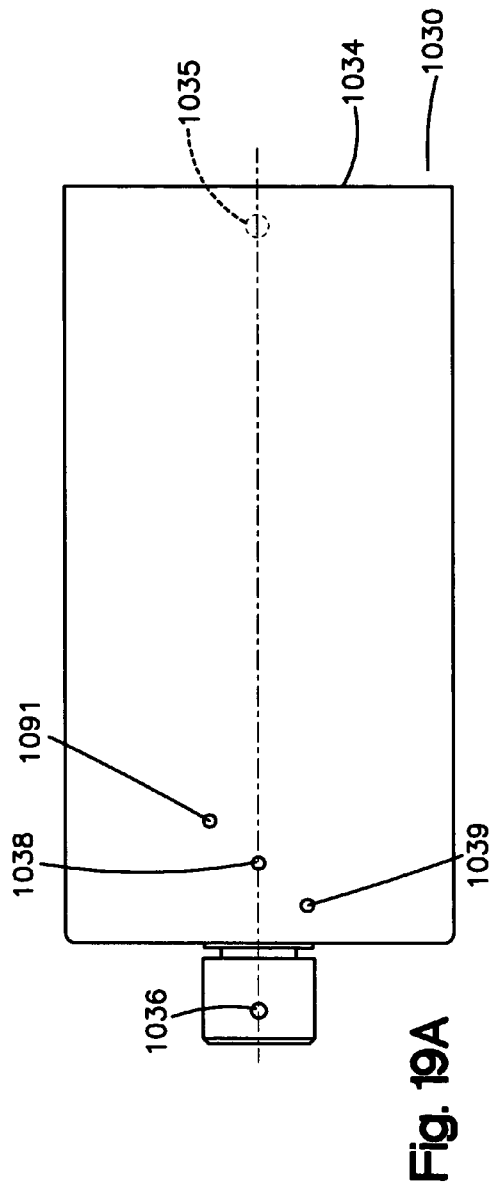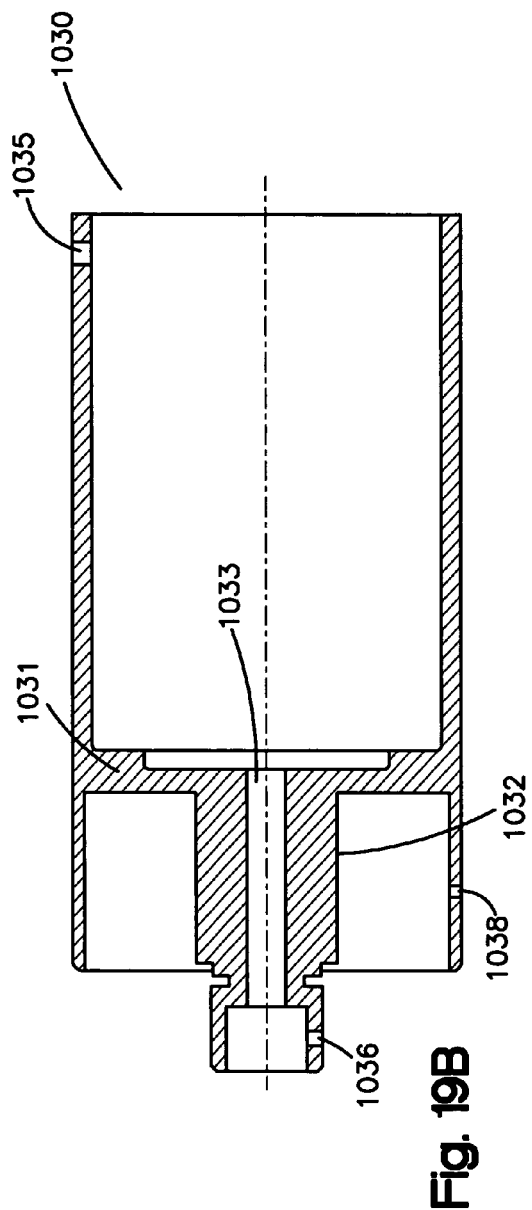
Fig. 19A
Fig. 19B

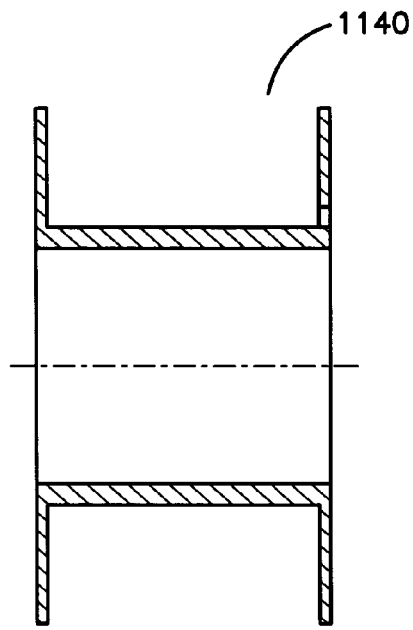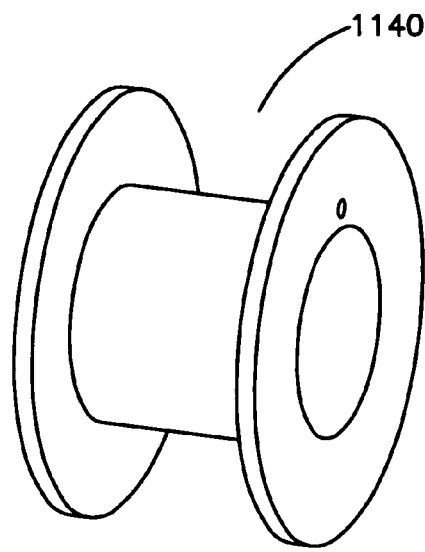
Fig. 20A    Fig. 20B
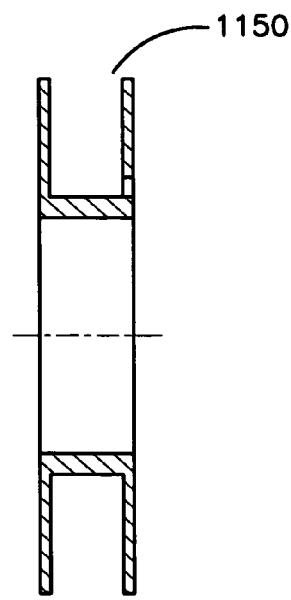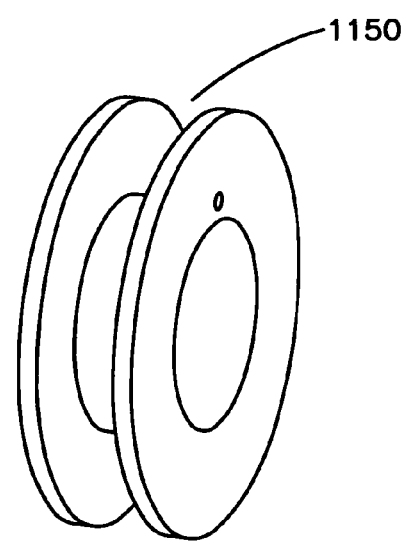
Fig. 21A    Fig. 21B

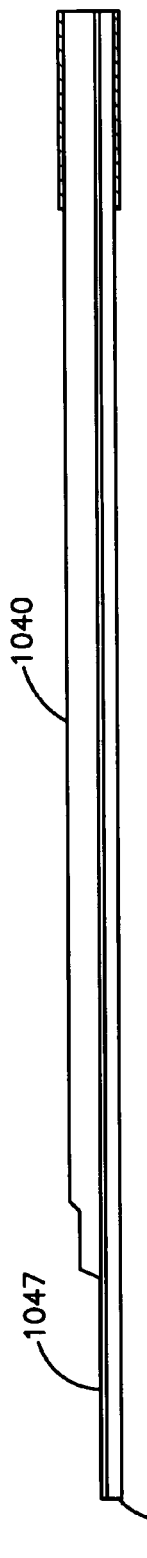
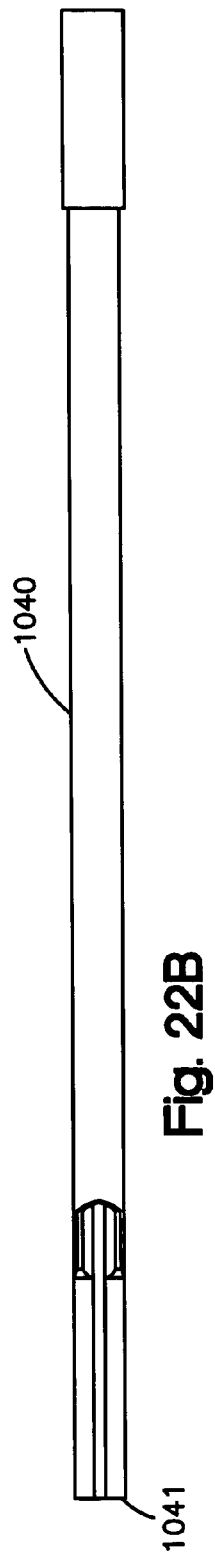
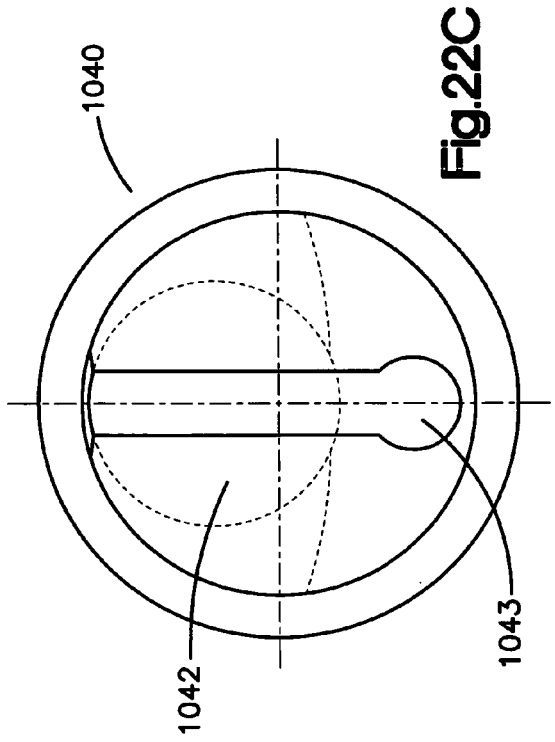
Fig. 22A
Fig. 22B
Fig. 22C

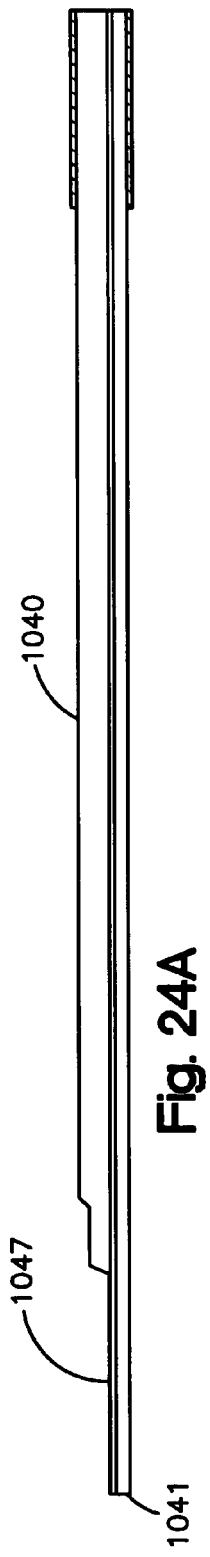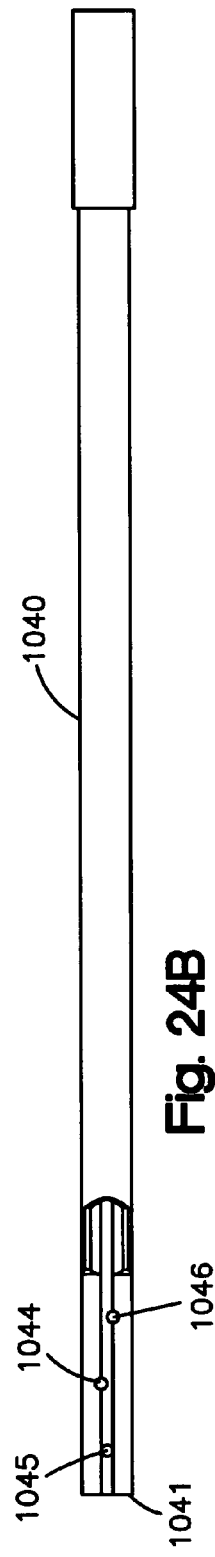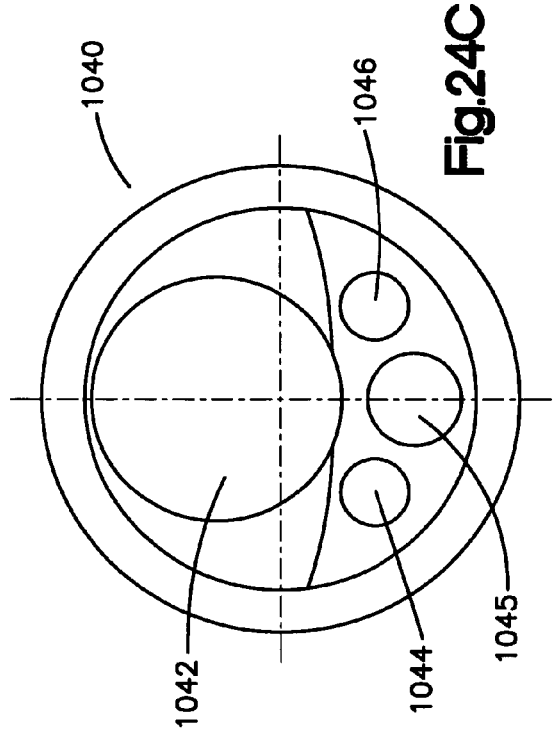

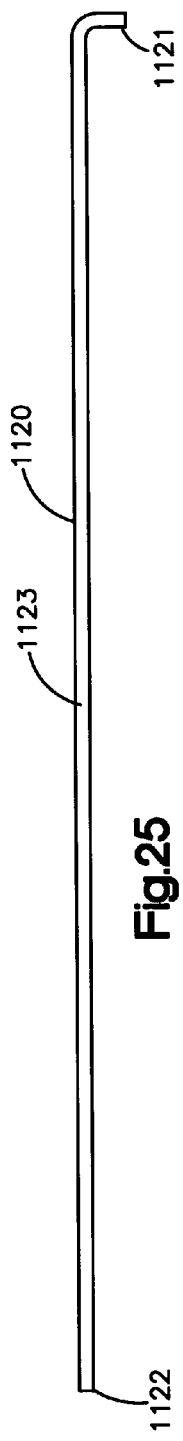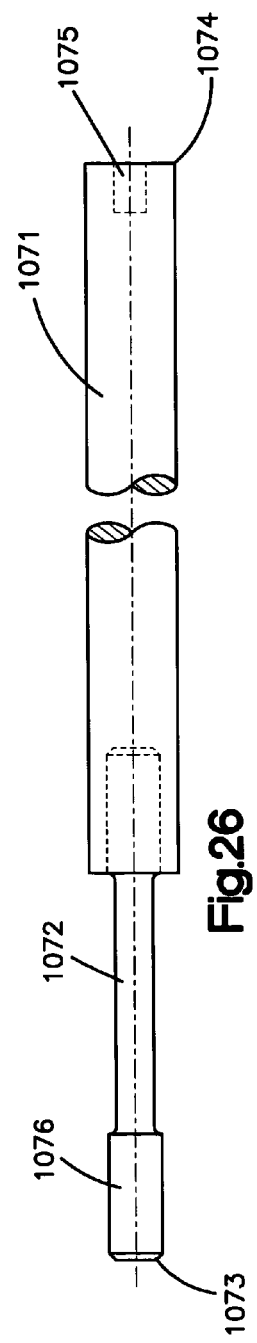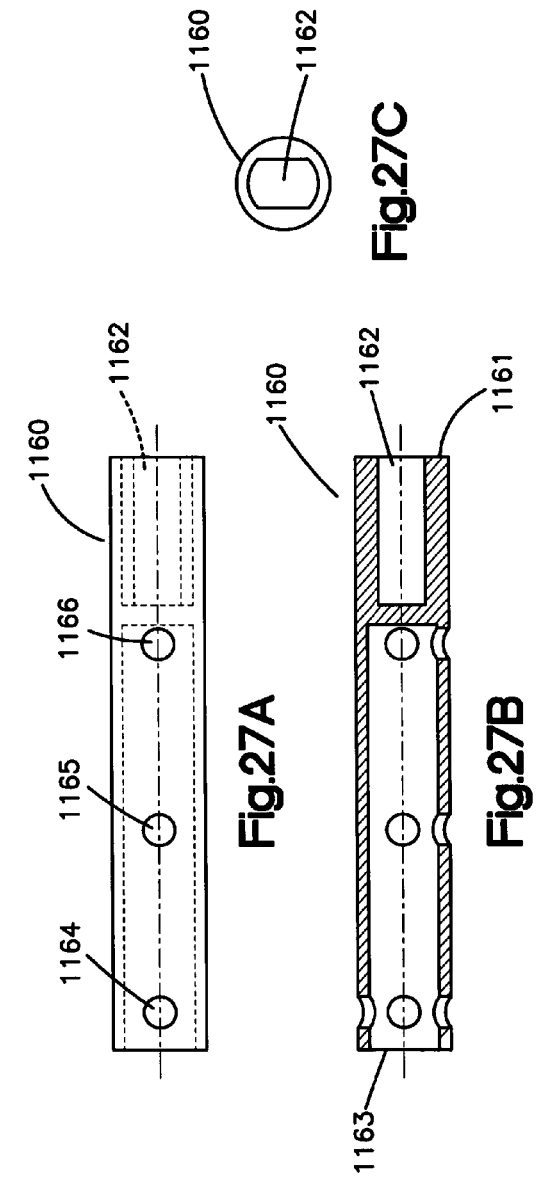

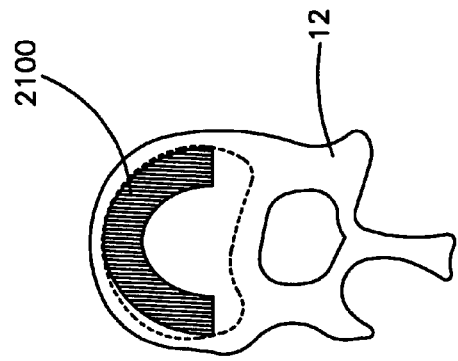
Fig. 32
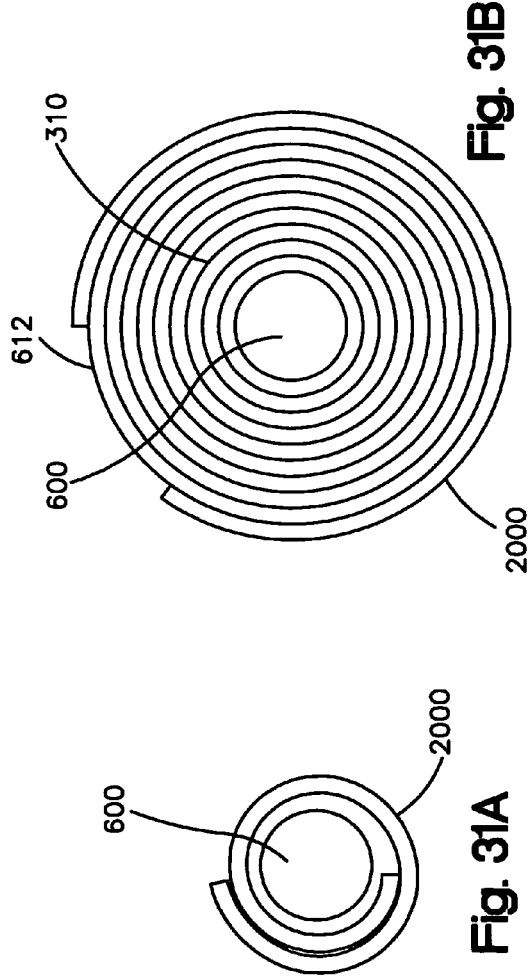
Fig. 31B
Fig. 33C
Fig. 33B
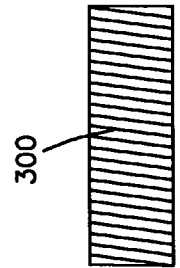
Fig. 33A

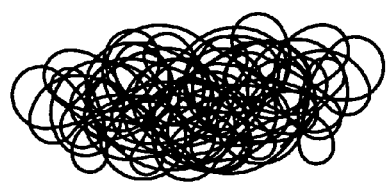
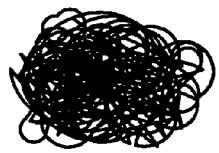
Fig. 35A  Fig. 35B
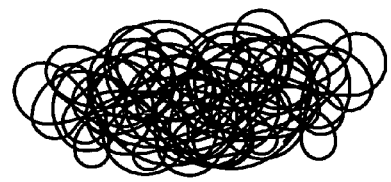
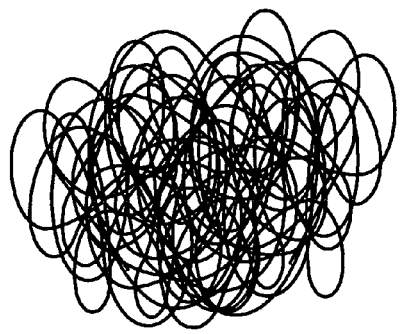
Fig. 36A  Fig. 36B
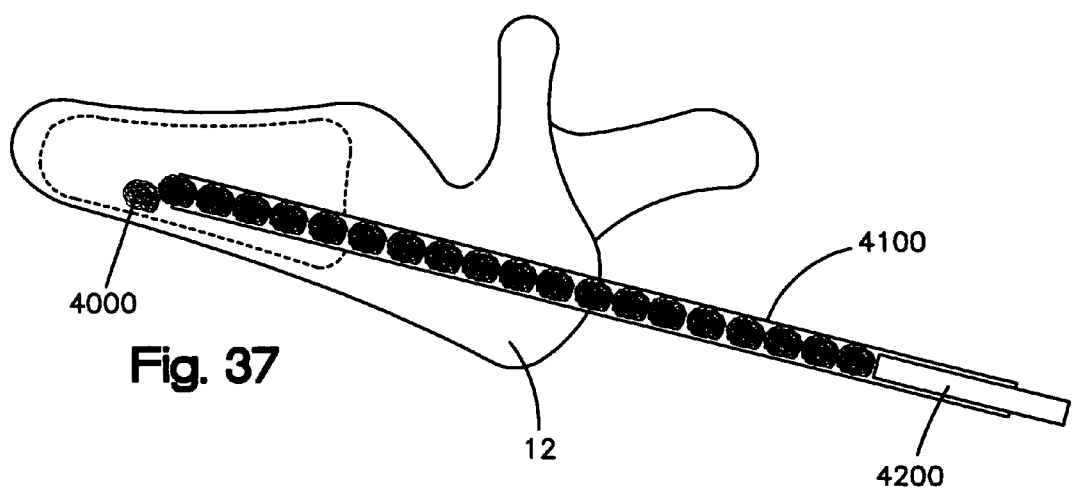
Fig. 37

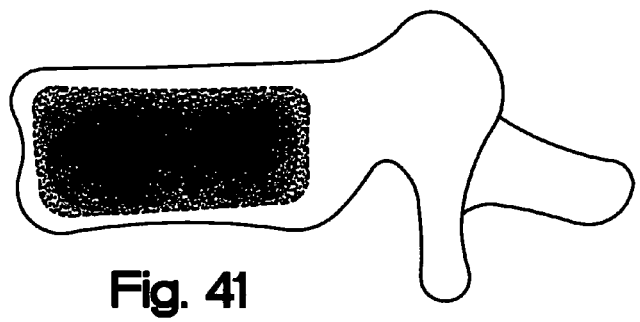
Fig. 41
  
Fig. 42A    Fig. 42B        Fig. 42C
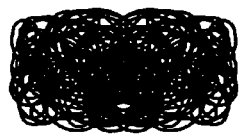   
Fig. 43A        Fig. 43B
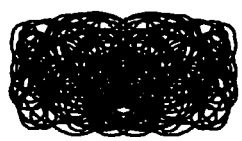   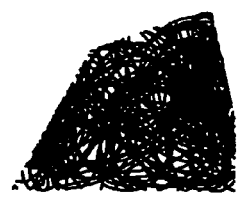
Fig. 43C        Fig. 43D

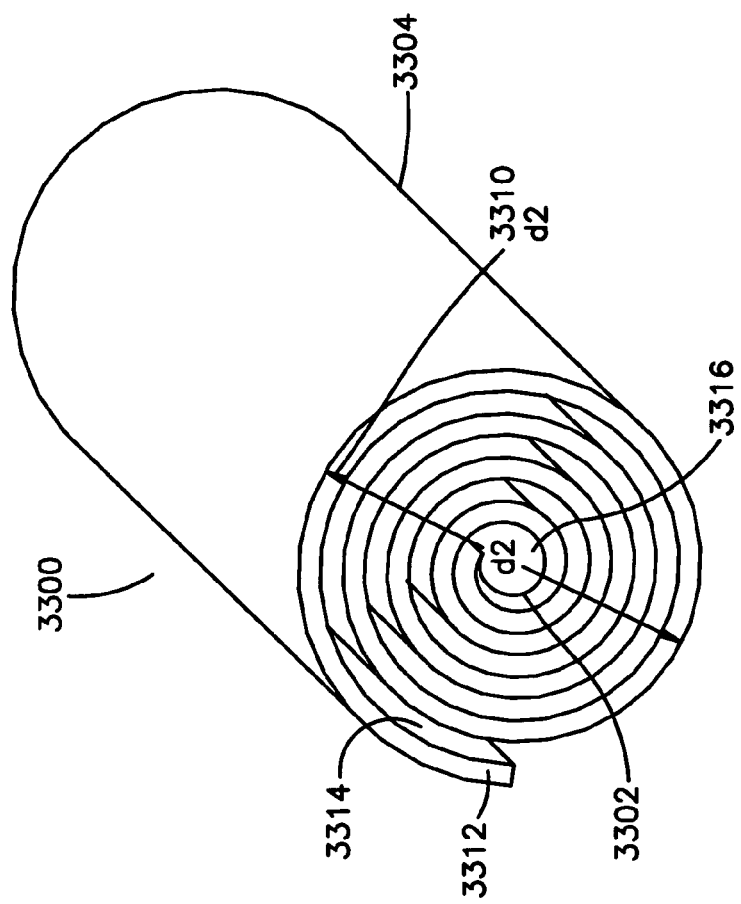
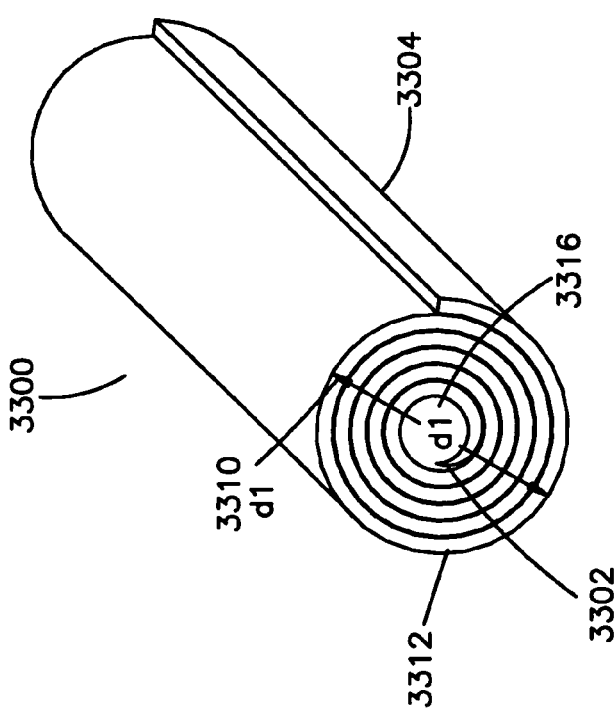

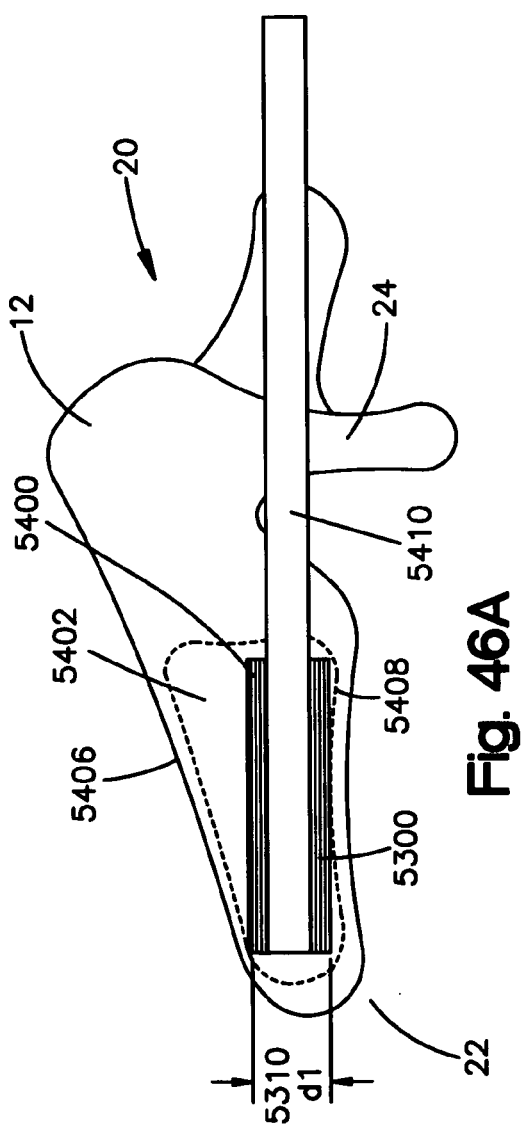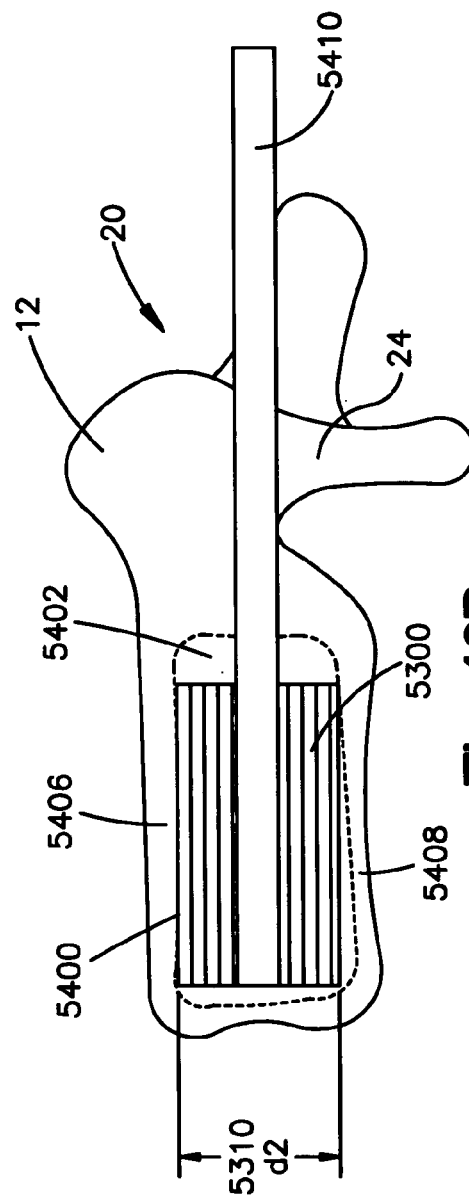
Fig. 46A
Fig. 46B

APPARATUS AND METHODS FOR TREATING BONE

CROSS REFERENCE TO RELATED APPLICATIONS

The present application claims priority to U.S. Provisional Application Nos. 60/692,408 filed Jun. 20, 2005; 60/715,188 filed Sep. 8, 2005; and 60/733,647 filed Nov. 4, 2005, the entire content of which are expressly incorporated herein by reference thereto.

FIELD OF THE INVENTION

The invention relates to surgical implants, and more particularly to minimally invasive apparatus and methods for treating (filling, augmenting, and/or reposition bone) bone, preferably vertebrae and/or restoring spinal lordosis.

BACKGROUND OF THE INVENTION

Vertebral compression fractures, as illustrated in FIG. 1, represent a generally common spinal injury and may result in prolonged disability. F. Margerl et al: A comprehensive classification of thoracic and lumbar injuries, *Eur Spine J* 184-201, 1994. These fractures involve collapsing of one or more vertebral bodies 12 in the spine 10. Compression fractures of the spine usually occur in the lower vertebrae of the thoracic spine or the upper vertebra of the lumbar spine. They generally involve fracture of the anterior portion 18 of the affected vertebra 12 (as opposed to the posterior side 16). Spinal compression fractures can result in deformation of the normal alignment or curvature, e.g., lordosis, of vertebral bodies in the affected area of the spine. Spinal compression fractures and/or related spinal deformities can result, for example, from metastatic diseases of the spine, from trauma or can be associated with osteoporosis. Until recently, doctors were limited in how they could treat such compression fractures and related deformities. Pain medications, bed rest, bracing or invasive spinal surgery were the only options available.

More recently, minimally invasive surgical procedures for treating vertebral compression fractures have been developed. These procedures generally involve the use of a cannula or other access tool inserted into the posterior of the effected vertebral body through the pedicles. The most basic of these procedures is vertebroplasty, which literally means fixing the vertebral body, and may be done without first repositioning the bone.

Briefly, a cannula or special bone needle is passed slowly through the soft tissues of the back. X-ray image guidance, along with a small amount of x-ray dye, allows the position of the needle to be seen at all times. A small amount of polymethylmethacrylate (PMMA) or other orthopedic cement is pushed through the needle into the vertebral body. PMMA is a medical grade substance that has been used for many years in a variety of orthopedic procedures. Generally, the cement is mixed with an antibiotic to reduce the risk of infection, and a powder containing barium or tantalum, which allows it to be seen on the X-ray.

Vertebroplasty can be effective in the reduction or elimination of fracture pain, prevention of further collapse, and a return to mobility in patients. However, this procedure may not reposition the fractured bone and therefore may not address the problem of spinal deformity due to the fracture. It generally is not performed except in situations where the kyphosis between adjacent vertebral bodies in the effected area is less than 10 percent. Moreover, this procedure requires high-pressure cement injection using low-viscosity cement, and may lead to cement leaks in 30-80% of procedures, according to recent studies. Truumees, Comparing Kyphoplasty and Vertebroplasty, *Advances in Osteoporotic Fracture Management*, Vol. 1, No. 4, 2002. In most cases, the cement leakage does no harm. In rare cases, however, polymethymethacrylate or other cement leaks into the spinal canal or the perivertebral venous system and causes pulmonary embolism, resulting in death of the patient. J. S. Jang: Pulmonary Embolism of PMMA after Percutaneous Vertebroplasty, *Spine* Vol. 27, No. 19, 2002.

More advanced treatments for vertebral compression fractures generally involve two phases: (1) reposition, augmentation or restoration of the original height of the vertebral body and consequent lordotic correction of the spinal curvature; and (2) filling or addition of material to support or strengthen the fractured bone.

One such treatment, balloon kyphoplasty (Kyphon, Inc.), is illustrated in FIGS. 2A-D. A catheter having an expandable balloon tip is inserted through a cannula, sheath or other introducer into a central portion of a fractured vertebral body comprising relatively soft cancellous bone surrounded by fractured cortical bone (FIG. 2A). Kyphoplasty then achieves the reconstruction of the lordosis, or normal curvature, by inflating the balloon, which expands within the vertebral body restoring it to its original height (FIG. 2B). The balloon is removed, leaving a void within the vertebral body, and PMMA or other filler material is then injected through the cannula into the void (FIG. 2C) as described above with respect to vertebroplasty. The cannula is removed and the cement cures to fill or fix the bone (FIG. 2D).

Disadvantages of this procedure include the high cost, the repositioning of the endplates of the vertebral body are lost after the removal of the balloon catheter, and the possible perforation of the vertebral endplates during the procedure. As with vertebroplasty, perhaps the most feared, albeit remote, complications related to kyphoplasty are related to leakage of bone cement. For example, a neurologic deficit may occur through leakage of bone cement into the spinal canal. Such a cement leak may occur through the low resistance veins of the vertebral body or through a crack in the bone which had not been appreciated previously. Other complications include; additional adjacent level vertebral fractures, infection and cement embolization. Cement embolization occurs by a similar mechanism to a cement leak. The cement may be forced into the low resistance venous system and travel to the lungs or brain resulting in a pulmonary embolism or stroke. Additional details regarding balloon kyphoplasty may be found, for example, in U.S. Pat. Nos. 6,423,083, 6,248,110, and 6,235,043 to Riley et al.; Gantis et al., Balloon kyphoplasty for the treatment of pathological vertebral compression fractures, *Eur Spine J* 14:250-260, 2005; and Lieberman et al., Initial outcome and efficacy of Kyphoplasty in the treatment of painful osteoporotic vertebral compression fractures, *Spine* 26(14):1631-1638, 2001, each of which is incorporated by reference herein in its entirety.

Another approach for treating vertebral compression fractures is the Optimesh system (Spineology, Inc., Stillwater, Minn.), which provides minimally invasive delivery of a cement or allograft or autograft bone using an expandable mesh graft balloon, or containment device, within the involved vertebral body. The balloon graft remains inside the vertebral body after its inflation, which prevents an intraoperative loss of reposition, such as can occur during a kyphoplasty procedure when the balloon is withdrawn. One drawback of this system, however, is that the mesh implant is not well integrated in the vertebral body. This can lead to relative motion between the implant and vertebral body, and consequently to a postoperative loss of reposition. Additional details regarding this procedure may be found, for example, in published U.S. patent Publication No. 20040073308, which is incorporated by reference herein in its entirety.

Still another procedure used in the treatment of vertebral compression fractures is an inflatable polymer augmentation mass known as a SKy Bone Expander. This device can be expanded up to a pre-designed size and Cubic or Trapezoid configuration in a controlled manner. Like the Kyphon balloon, once optimal vertebra height and void are achieved, the SKy Bone Expander is removed and PMMA cement or other filler is injected into the void. This procedure therefore entails many of the same drawbacks and deficiencies described above with respect to kyphoplasty.

A proposed improved procedure for repositioning and augmenting vertebral body compression fractures is vertebral body stenting, for example as described in Fürderer et al., "Vertebral body stenting", *Orthopäde* 31:356-361, 2002; European Patent Application publication number EP1308134A3; and United States patent application publication No. US2003/0088249, each of which is incorporated by reference herein in its entirety. Veterbral body stenting, as depicted for example in FIG. 3, generally involves inserting into a vertebral body a balloon-tipped catheter (e.g., such as a kyphoplasty balloon) surrounded by a stent (e.g., such as those used in angioplasty). After insertion of the balloon and stent, the balloon is inflated, e.g., using fluid pressure, thereby expanding the stent within the vertebral body. After expansion of the stent, the balloon may be deflated and removed, with the stent remaining inside the vertebral body in an expanded state to fill the vertebral body.

There remains a need for implants and related methods for repositioning and augmenting fractured vertebral bodies and other bones.

SUMMARY OF THE INVENTION

The present invention provides a bone treatment system, preferably a minimally invasive bone treatment system for filling, augmenting and/or repositioning bone, which may include a body or bobbin and a band configured to contact and coil around the bobbin and increase the diameter of the bone implant. In one embodiment the present invention provides an implant and method for correction of vertebral fractures and other disorders of the spine. For example, a cylindrical body or bobbin may be inserted into a vertebral body damaged by a vertebral compression fracture. After insertion of the bobbin, a wire, string, thread or band, collectively referred to herein as a "band", is coiled preferably multiple times around the bobbin. The band may have any profile or shape and may be comprised of any biocompatible material. During coiling, the diameter of the bobbin/band complex, sometimes referred to as a coiled bobbin assembly, may increase. Such increase in diameter can push against the inner side of the endplates of the vertebral body, and restore the vertebral body to its original height. Additionally, bone fragments or segments around the bobbin/band complex can be compacted during coiling of the band.

In some embodiments, features for controlling rotation of the bobbin head and/or coiling of the band can include a shaft, rod or cannula for rotating the bobbin, and a guide, guide conduit, cannula, tub for controlling and/or providing the band. The bobbin can have various configurations, multiple joints and/or can be bendable.

In other embodiments, minimally invasive implants for distracting spine segments include an elongated body having an end dimensioned for implantation in a space between two or more vertebral features, and a band associated with and configured to coil around the body to increase a diameter of the end and thereby increase the space between the two or more vertebral endplates, bone segments, or spinous processes.

In another embodiment, a kit comprises various combinations of assemblies and components according to the present invention. For example, a kit may include, for example, an insertion device, a bobbin, and a band according to the present invention.

In a further embodiment, a system for bone treatment (filling, augmenting, and/or reposition bone), preferably minimally invasive osteopathic treatment may comprise a bobbin having a diameter, and a first and second end, the bobbin configured for implantation within a bone, and a band having a length substantially larger than its width or height, the band configured to contact and coil multiple times around the bobbin between the first and second end to increase the diameter of the bobbin when the bobbin is implanted within bone. The system may further comprise an elongated body having a proximal end and a distal end, the proximal end configured for manipulation by a user outside the patient to place the distal end in a desired position within the bone, and a joint disposed between the second end of the bobbin and the distal end of the elongated body. The bobbin is cylindrical and comprises a hole through which a portion of said band passes.

The elongated body may comprise at least a portion of a drive line assembly to rotate the bobbin when the bobbin is implanted within bone. The elongated body is configured to rotate, and the joint is configured to transfer rotation from the elongated body to rotate the bobbin. The joint is releasable so that the elongated body can be detracted from the bobbin.

The system may further comprise a guide mechanism configured to control the position of the band between the first and second end of the bobbin when the band is coiled around the bobbin, a drive line assembly configured to releasably attach to and rotated the bobbin having a proximal end and a distal end, the proximal end configured in use to extend from the patient and be manipulated by a user to place the distal end in a desired position in the bone, the distal end releasably connected to the bobbin. The drive line assembly is rotatable to rotate the bobbin when the bobbin is located in the bone. The guide mechanism may comprise a guide moveable with respect to the bobbin to control the position of the band between the first and second ends when the band is coiled around the bobbin.

The drive line assembly may comprise a rotatable shaft and the guide mechanism may comprise an elongated tube coaxial with the rotatable shaft. The elongated tube is moveable in an axial direction relative to the bobbin and contacting the band to position the band between the first and second ends of the bobbin.

The system may also comprise a knob connected to the elongated tube and containing a guide hole for the band.

The bobbin may have threads to assist in guiding the band.

In an alternative, the drive line assembly may comprise a rotatable shaft having a proximal end and a distal end, where the distal end of the shaft is releasably and rotatably connectable to the first end of the bobbin. The shaft being capable of transferring torque to the bobbin. The guide mechanism, in the alternative may comprise a guide tube having a proximal end and a distal end through which the band moves, the guide tube movable axially with respect to the shaft.

The rotatable shaft and guide tube may be located in a needle, such that the rotatable shaft is axially fixed with respect to the needle and the guide tube moves axially with respect to the needle. A portion of the needle may be positioned along side and adjacent the bobbin.

The system may also comprise a drive train to convert the rotary motion of the drive line assembly to an axial motion, the drive train connectable to the drive line assembly and the guide tube to move the guide tube axially. The drive train may comprise a gear connectable with the rotatable drive train, a rotatable cam disk and an axially moveable but non-rotatable follower. The cam disk having a groove along its outer surface and the follower including a projection, where the projection extends into the groove.

The follower may be a spool holder and the projection a dowel pin insertable through a hole in the spool holder.

The band may be coated with or form part of a matrix with other materials to include osteo-inductive materials, osteo-conductive materials, antibiotics, tricalcium phosphate, bone morphogenetic proteins.

In an another embodiment a system for minimally invasive bone treatement, filling, augmenting, and/or reposition bone, may comprise an elongated body having a first end and a second end, the body having a length along its longitudinal axis, configured for implantation within a bone, and an insertion device for inserting the elongated body within a bone, the insertion device comprising a band and configured to cause the band to coil multiple times around the elongated body between the first and second end to increase the diameter of the body and band assembly, the insertion device releasably connectable to the body. The insertion device may comprise a drive line assembly to apply a rotational force to the elongated body to cause the elongated body to rotate about its longitudinal axis to coil the band around the elongated body, to increase the diameter of the elongated body and band assembly implanted within the region of bone.

The system may further comprise an axial guide mechanism movable axially with respect to the elongated body, the axial guide mechanism in connection with and controlling the position of the band along the length of the elongated body as it rotates.

The drive line assembly may comprise a rod connected to the elongated body, the rod being rotatable which in turn rotates the elongated body. The guide mechanism may comprise an outer cannula, causing the band to reposition along the length of the elongated body. Continued rotation of the elongated body causes the diameter of the elongated body and band assembly to increase due to the coiling of the band around the elongated body.

In the alternative, the drive line assembly may comprise a drive mechanism, a drive shaft, and a flexible shaft connected serially to the elongated body, and the guide mechanism may comprise a band guide conduit, a spool holder, and a rotatable cam disk. The cam disk and spool holder converts the rotational force of the cam disk to an oscillating force applied to the band guide conduit causing the band guide conduit to move forward and backward relative to the elongated body. The band guide conduit may comprise an interior passage way having a proximal and distal opening and wherein the band is positioned in and moves through the interior passage way of the band guide conduit out the distal opening where it coils around the body.

The insertion device may further comprise a drive train to couple the drive shaft of the drive line assembly to the cam disk of the guide mechanism so as to have the cam disk rotate at a different velocity than the drive shaft, where the drive train comprises a drive gear, a sprocket, and another gear.

In a further embodiment, a system for minimally invasive bone treatment, filling, augmenting, and/or repositioning, may comprise an elongated body having a first end and a second end. The body having a length along its longitudinal axis, is configured for implantation within a bone. The system may further include an insertion device for inserting the elongated body within a bone. The insertion device may comprise a band and configured to cause the band to coil multiple times around the elongated body between the first and second end to increase the diameter of the body and band assembly, the insertion device releasably connectable to the body. The insertion device may further comprise a drive line assembly to apply a rotational force to the elongated body to cause the elongated body to rotate about its longitudinal axis to coil the band around the elongated body, so as to increase the diameter of the elongated body and band assembly implanted within the region of bone. The drive line assembly may comprise a drive mechanism, a drive shaft and a flexible shaft connected serially to the first end of the elongated body. The insertion device may further include an axial guide mechanism movable axially with respect to the elongated body. The axial guide mechanism in connection with and controls the position of the band along the length of the elongated body as it rotates. The guide mechanism may comprise a band guide conduit, a spool holder, and a rotatable cam disk, where the cam disk has a groove along its outer surface and the spool holder including a projection where the projection extends into the groove of the cam disk. The insertion device may also include a drive train coupling the drive shaft of the drive line assembly to the cam disk of the guide mechanism so as to have the cam disk rotate at a different velocity than the drive shaft. The drive train may comprise a drive gear, a sprocket, and another gear. The cam disk and spool holder converts the rotational force of the cam disk to an oscillating force applied to the band guide conduit causing the band guide conduit to move forward and backward relative to the elongated body, and the band guide conduit comprises an interior passage way having a proximal and distal opening and wherein the band is positioned in and moves through the interior passage way of the band guide conduit out the distal opening where it coils around the body. The flexible shaft and band guide conduit are located in a needle, such that the flexible shaft is axially fixed with respect to the needle and the band guide conduit moves axially with respect to the needle. A portion of the needle is positioned along side and adjacent the bobbin, and continued rotation of the elongated body causes the diameter of the elongated body and band assembly to increase due to the coiling of the band around the elongated body.

In a further embodiment, the present invention provides an implant and method for correction of vertebral fractures and other disorders of the spine. For example, one or more wool bales or fibrous massesibodies may be inserted into a vertebral body damaged by a vertebral compression fracture. As the fibrous bodies are inserted into a vertebral body, they may fill a central portion of the vertebral body and may push against the inner sides of the endplates of the vertebral body, thereby providing structural support and tending to restore the vertebra to its original height. Optionally, the fibrous masses may comprise a shape-memory alloy or other material that expands or changes configuration after implantation, which may lead to a thorough integration of the implant into the bone and/or help restore the height of the damaged vertebral body. After implantation, a bone cement (e.g., PMMA or tricalcium phosphate), bone chips, demineralized bone, or other filler material or implant may be added with or without the implanted fibrous mass to aid in stabilizing the bone and securing the implant in place within the bone.

The fibrous masses may be comprised of a thread or other relatively thin structure, for example a fiber or strand, of any biocompatible material having desired characteristics, for example a shape memory alloy (e.g., nitinol or other nickel-titanium alloy, copper-based alloys, iron-based alloys, etc.), titanium, stainless steel, a biocompatible polymer, another metal or metal alloy, a ceramic, a composite or any combination thereof. The, strand, thread or other fiber may be coiled, woven, matted, tangled or otherwise formed into a wool-like mass or body having a desired configuration. The bodies may be individually inserted into a bone, or may be joined or linked in series to form a chain having desired characteristics of flexibility, strength, and the like. In some embodiments, the bodies and/or links may be resorbable.

In another embodiment, a kit may comprise various combinations of components according to the present invention. A kit may include, for example, a cannula and one or more fibrous body implants. A kit may additionally include a syringe or other apparatus for injecting a cement or other filler into a vertebral body. Optionally, one or more other implants, devices may be included in a kit.

Another embodiment provides implants for minimally invasive osteopathic treatment (filling, augmenting, and/or reposition bone), which may include a body comprising a sheet coiled multiple times. The body, having a first diameter, is configured for implantation within a bone. The body is also configured to expand to a second diameter by uncoiling the sheet when the body is implanted in the bone. Insertion of the body into bone can be accomplished using a sheath or cannula.

The sheet may comprise any of stainless steel, a nickel titanium alloy, a cobalt alloy, another metal alloy, a polymer, or a combination thereof.

The system may further include an axial member, having a first end and second end that is substantially cylindrical, where the body may be coiled around the axial member. The axial member comprises a lumen through which a filler material can be injected into the bone.

In a further embodiment, the sheet may comprise a plurality of holes, where the holes are dimensioned to allow the filler material to penetrate the body In still a further embodiment, the axial member may be rotated in a direction opposite of the coiling of the body to expand the body by partially uncoiling the coiled sheet.

In still another embodiment, the present invention provides an implant and method for correction of vertebral fractures and other disorders of the spine. For example, a coiled sheet may be inserted into a vertebral body damaged by a vertebral compression fracture. After insertion into a damaged vertebral body, the coiled sheet can be uncoiled to expand its diameter. Such increase in diameter can push against the inner side of the endplates of the vertebral body, and tend to restore the vertebral body to its original height. Additionally, uncoiling of the sheet can compact the bone around the implant, which can lead to a better integration of the implant in the bone. The coiled sheet may be comprised of any biocompatible material having desired characteristics, for example stainless steel, aluminum, a metal alloy, e.g., a cobalt alloy, a nickel titanium alloy or another alloy, a polymer, or any combination thereof.

In some embodiments, a method of treating bone can include inserting inside a fractured bone, for example a vertebrae, a device comprising a sheet of material coiled around an axial member, causing the coiled sheet to partially uncoil from around the axial member to increase the diameter of the device and to apply a radial force to move the fractured bone into a desired position. After repositioning, the implanted device can be removed from the bone, or some or all of the device can be left inside the bone to maintain the desired position. In addition, a bone cement or other filler may be added with or without the implanted device to aid in stabilizing the bone.

In some embodiments, an expandable body comprises a fenestrated sheet coiled about a shaft, or axial member. The fenestrated sheet includes holes that can allow passage of bone cement or other material injected into the expandable body to further treating a vertebral body or other bone into which the expandable body is inserted. The bone cement or other filler material can be injected, for example, through a lumen of the axial member, for example using a syringe or other device.

In other embodiments, a coiled sheet includes perforations, hinge features or other joints that define the sheet into a plurality of adjacent planes, or segments. Such joints can provide incremental increases in diameter of the coiled body. Moreover, the joints allow use of more rigid materials for the sheet, and the joints provide discrete locations for the sheet to bend, e.g., between segments. In some embodiments, use of substantially rigid or stiff materials can provide for increased radial (e.g., outward) forces during uncoiling in a confined area such as within a vertebral body.

In other embodiments, minimally invasive implants for distracting spine segments include a coiled body having a first diameter dimensioned for implantation in a space between two or more vertebral features, wherein the coiled body is configured to uncoil to a second diameter that is larger than the first diameter, and thereby increase the space between the two or more vertebral features.

In another embodiment, a kit comprises various combinations of assemblies and components according to the present invention. A kit may include, for example, a cannula and a coiled body according to the present invention. In other embodiments, a kit may include a cannula, a coiled body, and a syringe or other apparatus for injecting a cement or other filler into a vertebral body.

BRIEF DESCRIPTION OF THE DRAWINGS

The invention is explained in even greater detail and may be better understood by the following exemplary drawings, wherein like references numerals represent like elements. The drawings are merely exemplary to illustrate certain features that may be used singularly or in combination with other features and the present invention should not be limited to the embodiments shown.

FIGS. 7A and B are cross-sectional side top view illustrations of an apparatus and method employing a band guide according to an embodiment of the present invention;

FIG. 8 is a detailed cross-sectional side view of an apparatus of FIGS. 7A and B;

FIG. 9 is a cross-sectional top view illustration of another embodiment of an apparatus and method according to the present invention;

FIG. 10 is an illustration of an embodiment of an insertion device and bobbin according to the present invention;

FIG. 11 is an illustration of another embodiment of an insertion device and bobbin according to the present invention;

FIGS. 14A and B are cross-sectional views of the housing of the insertion device depicted in FIG. 11;

FIGS. 15A and B are an end view and a side view of the end cap of the insertion device depicted in FIG. 11;

FIG. 16 is a cross-sectional view of the sprocket of the insertion device depicted in FIG. 11;

FIGS. 17A and B are cross-sectional views of the drive shaft of the insertion device depicted in FIG. 11;

FIG. 18 is a cross-sectional view of the cam disk of the insertion device depicted in FIG. 11;

FIG. 19A is a side view of the spool holder of the insertion device depicted in FIG. 11

FIG. 19B is a cross-sectional view of the spool holder of the insertion device depicted in FIG. 11;

FIG. 20A is a cross-sectional top view of a large band spool of the present invention;

FIG. 20B is perspective view of a large band spool of the present invention;

FIG. 21A is a cross sectional view of a small band spool of the present invention;

FIG. 21B is a perspective view of a small band spool of the present invention;

FIGS. 22A-C are cross-sectional side views and an end view of an embodiment of a needle of the present invention;

FIGS. 24A-C are cross-sectional side views and a end view, respectively of an embodiment of a needle of the present invention;

FIG. 25 is a cross-sectional view of a band guide conduit of the present invention;

FIG. 26 is a cross-sectional view of a flexible shaft of the present invention;

FIGS. 27A-C are detailed cross-sectional side views and an end view, respectively of a bobbin of the present invention;

FIGS. 31A and B are cross-sectional end views of another embodiment of an expandable osteopathic augmentation apparatus according to an embodiment of the present invention;

FIG. 32 is a cross-sectional top view of a flexible bobbin according an embodiment of to the present invention;

FIGS. 33A-C are illustrations depicting different bobbin configurations according to embodiments of the present invention;

FIGS. 35A and B are illustrations depicting wool bales (or fibrous masses/bodies) of different shapes;

FIGS. 36A and B are illustrations depicting wool bales before expansion and after expansion;

FIG. 37 is an illustration depicting insertion of fibrous masses with a cannula and insertion device;

FIG. 41 is an illustration depicting a vertebral body filled with expanded fibrous masses and bone cement;

FIGS. 42A-C are illustrations depicting linked wool bales or fibrous masses according to an embodiment of the present invention;

FIGS. 43A-D are illustrations depicting different configuration of wool bales or fibrous masses/bodies of shape-memory alloy;

FIGS. 45A and B are perspective view illustrations of a coiled body of an expandable augmentation device according to an embodiment of the present invention;

FIGS. 46A and B are cross-sectional side view illustrations of an augmentation device in a vertebral body according to a method of the present invention;

DETAILED DESCRIPTION

A vertebral body may be filled, augmented, or repositioned through insertion of one or more implants into an internal portion of the vertebral body, between the endplates of two adjacent vertebral bodies, or in other bone, e.g., a femur. In one embodiment, a vertebral body implant may comprise a bobbin with a thread, string, or wire, collectively referred to herein as a band 310, coiled around the bobbin to create a larger diameter mass or body, sometimes referred to as a coiled assembly, coiled band assembly, coiled body, final implant, or implant. The bobbin with the attached band may be inserted into the vertebral body through, for example, transpedicular access canals having a diameter of about 5 mm.

Figure 2B:
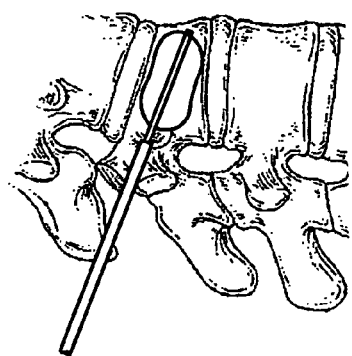
FIGS. 2A-D are illustrations of a prior art method for treating a vertical compression fracture.
Figure 2D:
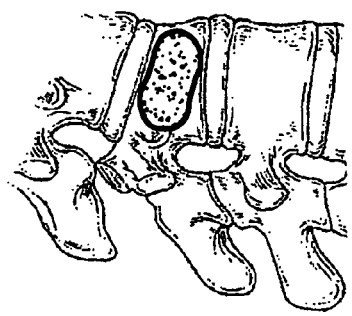
Figure 2A:
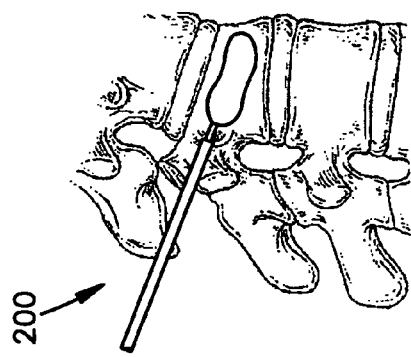
Figure 2C:
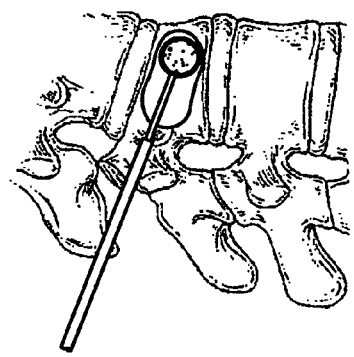
Figure 1:
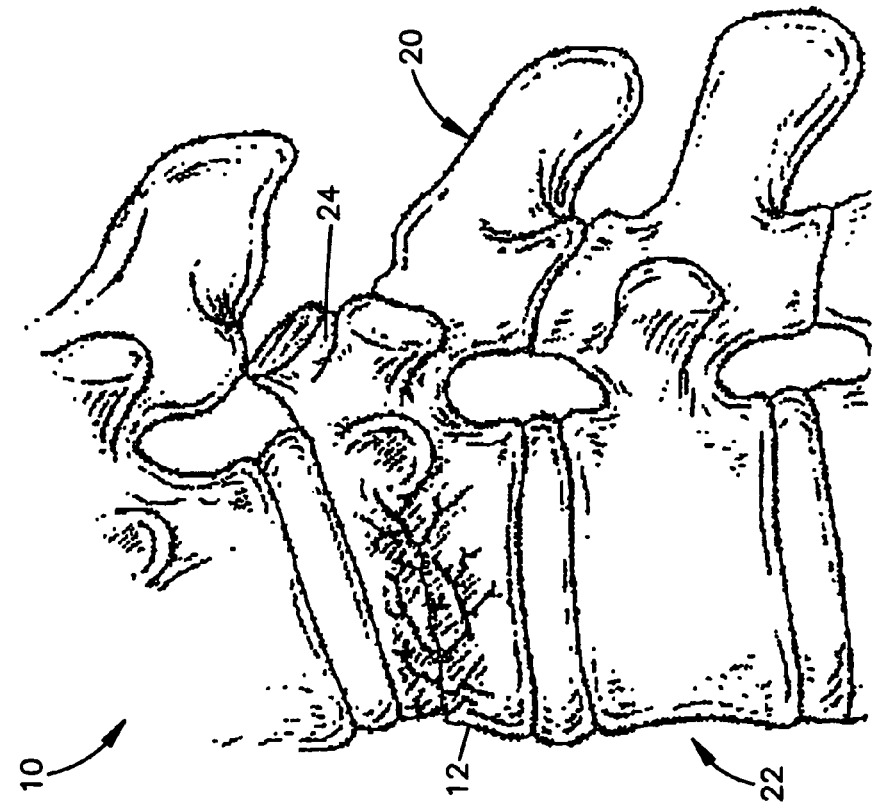
FIG. 1 is an illustration of a spine having a vertical compression fracture in one vertebral body.
Figure 3A:
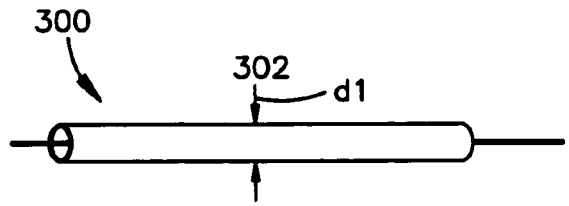
FIGS. 3A and B are side view illustrations of a bobbin and band apparatus according to an embodiment of the present invention.
Figure 3B:
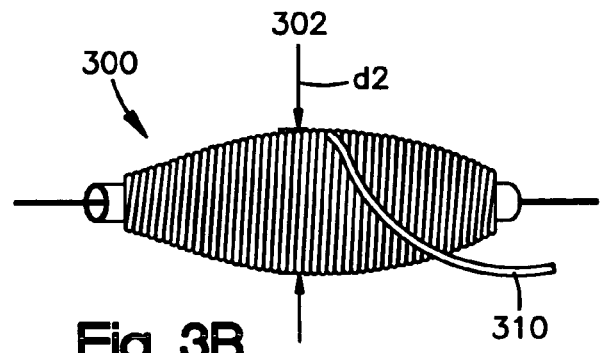

Referring to FIG. 3A, an elongated member 300, which may be cylindrical and is hereinafter referred to as a bobbin 300, has a certain diameter d1 302. After insertion of bobbin 300 into a collapsed vertebral body, band 310 is coiled around bobbin 300 to create a larger bobbiniband mass 312 also referred to as final implant 312 as shown in FIG. 3B. Such coiling may be performed by rotation of bobbin 300, by movement of band 310 around bobbin 300, or by any combination thereof. Band 310 can have different shapes and different sizes, and may be made of any biocompatible and preferably pliable material. The length of the band may be substantially larger than its width or height. One or more particular shapes of bands can be used to create any desired shape configuration of the coil band assembly depending upon the desired application. The band 310 may be comprised of different materials, such as nylon, polymers, metals, and the like. Band 310 may be radio opaque, such as suture material, metal, metal coated with bone cement, metal with a bone cement surface, metal with a polymer surface to allow welding the bobbin and the surrounding tissue together for reduction of bone micro-movement after augmentation, and natural fiber including a metal wire. The band may be woven, twisted, solid, tubular, or any other known type. The band preferably should be able to resist tension, preferably above 100 N and preferably withstand transversal pressure without significant deformation. The band preferably should further be able to slide along the tissue within the vertebral body but not along the bobbin. The band 310 may be coiled with or form part of a matrix with other materials, such as osteo-inductive materials, osteo-conductive materials, antibiotics, bone cement, bone chips, hypoxiapitate, tricalcium phosphate, bone morphogenetic proteins (BMG), etc. For spinal stenosis, the band preferably may preferably be coated with a material that inhibits bone fusion, while for application in between vertebral endplates the band, as an interbody fusion device, may preferably promote bone growth and integration.

Heating mechanisms for melting the band coating may be ultra-sound or an electric current, although other methods for melting the band coating are contemplated.

During coiling, diameter 302 of coiled band assembly 312 is increased to a desired size d2. Moreover, the diameter 302 of the implant can be varied along the length of the bobbin to tailor the size and shape of the implant.

Figure 4A:
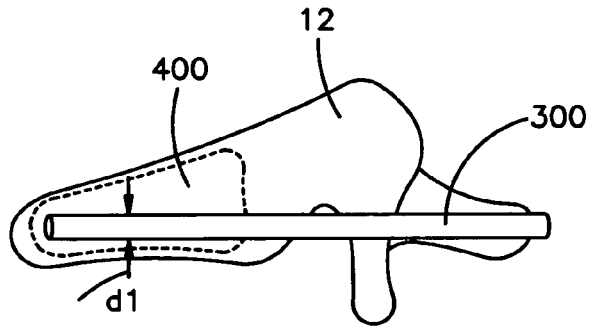
FIGS. 4A and B are cross-sectional side view illustrations of an apparatus and method for minimally invasive osteopathic treatment of a vertebral body according to an embodiment of the present invention.
Figure 4B:
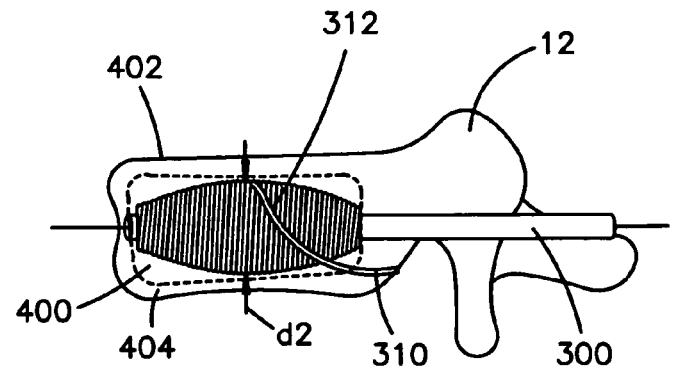

Referring to FIGS. 4A and 4B, bobbin 300 is inserted into a central portion 400 of vertebral body 12, for example through a cannula or other introducer. Suitable procedures and materials used for inserting a cannula through which bobbin 300 may be introduced are known in the art and may be similar to those described above for kyphoplasty and other procedures. For example, bobbin 300 may be introduced through the posterior portion 20 of the vertebral body 12. After bobbin 300 is inserted, a band 310 may be wound around bobbin 300 to form coiled band assembly 312. By increasing the diameter 302 of bobbin 300, endplates 402, 404 of vertebral body 12 may be pushed apart and the vertebral body may be restored to its original height (FIGS. 4A and 4B). Additionally, the bone around bobbin 300 may get compacted during the coiling of the thread or band 310.

Figure 5A:
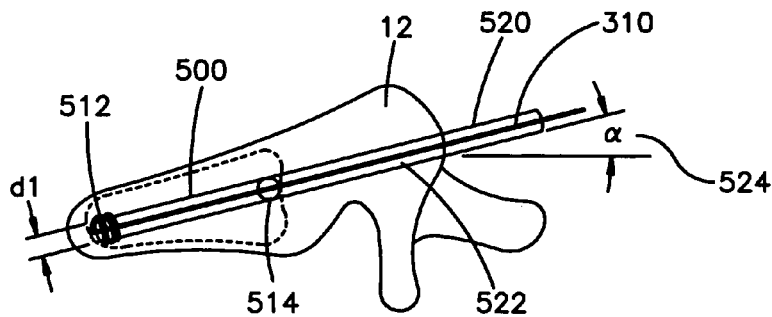
FIGS. 5A and B are cross-sectional side view illustrations of another embodiment of an apparatus and method according to the present invention.
Figure 5B:
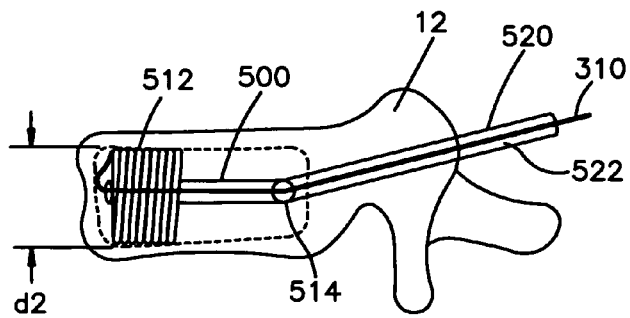

In some embodiments, the bobbin can include one or more joints to provide the surgeon the possibility to insert and/or arrange the bobbin at any angle α or other orientation. FIG. 5A depicts a bobbin with one joint 514 before augmentation of body 12, and FIG. 5B depicts a bobbin with one joint 514 after augmentation. Band 310 may pass through a passageway 522 in shaft 520 of bobbin 500 before coiling into coiled band assembly 512.

Figure 6A:
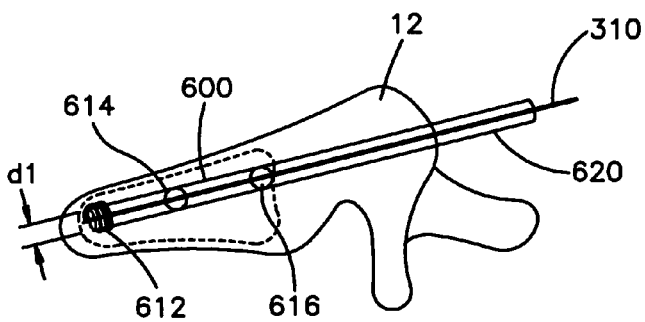
FIGS. 6A and B are cross-sectional side view illustrations of another embodiment of an apparatus and method according to the present invention.
Figure 6B:
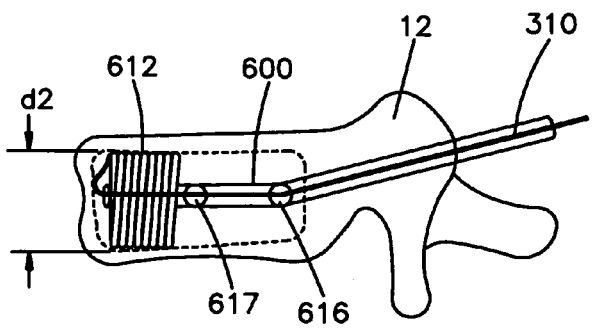

FIGS. 6A and B illustrate the use of a bobbin 600 having two joints 614, 616 for positioning and orienting bobbin 600 within vertebral body 12. FIG. 6A shows articulated bobbin 600 before augmentation and FIG. 6B shows enlarged bobbin implant 312 after coiling of band 310 around bobbin 600 within vertebral body 12. In some embodiments, as shown in FIGS. 5 and 6, band 310 may be inserted through a central passage or lumen in shaft 520, 620 of bobbin 500, 600, respectively.

Referring to FIGS. 7A and 7B, coiling of band 310 may be facilitated using a guide 700, also referred to herein as a slider 700. For example, as shown in FIG. 7A, bobbin 500 having a slider 700 may be inserted into vertebral body 12 through a cannula 710. Bobbin 500 may have a joint 514 that allows articulation of the end 512 of bobbin 500, with respect to shaft 520. Slider 700 can move, either in a uniform or predefined pattern, or manually as controlled by a user, with respect to bobbin 500 to guide coiling of band 310 over bobbin to expand size of implant 512 and define its shape.

As shown in FIG. 7B, guide 700 may be incorporated with a bobbin assembly having two or more joints, for example bobbin 600 having two joints. Bobbin 600 can be inserted into a vertebral body 12 through a cannula 710, and band 310 may pass through shaft 620 of bobbin 600. Band 310 engages slide 700 which cooperates with bobbin 600 to guide band 310 around bobbin 600 and increase the size of coil 612. Joints 614 and 616 allow articulation of bobbin 600 into a desired position and orientation for augmentation of vertebral body 12.

In some embodiments, head 602 of bobbin 600 and/or coil 612 remains in vertebral body 12 after the cannula 710 and shaft 620 of bobbin are removed from the patient to augment the vertebra and maintain proper lordosis. In other embodiments, PMMA or another cement or filler is inserted into vertebral body 12 along with bobbin coil 612 to further enhance fixation or repair of the damaged region. In other embodiments, bobbin 600 and/or bobbin coil 612 are removed after repositioning the bone and PMMA or another filler is injected into a void created by coil 612.

FIG. 8 is a detailed cross-sectional view of a bobbin, e.g., bobbin 500, having a guide or slider 700 to facilitate coiling of band 310. As described above, bobbin 500 may be inserted through cannula 710 and may include one or more joints 514 to facilitate positioning of coil 512. Slider 700 may include a head 703 that manipulates band 310 and cooperates with bobbin 500 to control the wrapping of band 310 to enlarge coil 512. Slider 700 may employ a screw or other mechanism to provide uniform coiling or a predefined coil pattern, and/or slider may be configured to be manipulated by a user to provide any desired pattern and shape of bobbin coil 512, e.g., to optimize engagement of coil 512 with inner walls of vertebral body 12. Slider 700 may pivot, bend or slide, or a combination of movements to facilitating placing of band 310 about bobbin 500. Slider 700 may pass through cannula 710 outside of bobbin, as shown in FIG. 8. In other embodiments, slider 700 may attach to and/or pass through shaft 520 of bobbin 500, may attach to cannula 710, or may be introduced into vertebra through another cannula or introducer.

Band 310 may pass through cannula 710 as shown in FIG. 8. In other embodiments, band 310 may pass through bobbin shaft 520. In other embodiments band 310 can be inserted through a cannula different than the cannula through which the bobbin is inserted. For example, as shown in FIG. 9, bobbin 600 having two joints 614 and 616 and slide 700 can be inserted into vertebral body 12 through a first cannula 710, while thread 310 can be inserted into vertebral body 12 through a second cannula 900.

FIG. 10 depicts in more detail various components of an embodiment of a bobbin 800 attached to an insertion device 810. In this embodiment, the band 310 may spool about a bobbin 800 due to rotational forces created by a drive line assembly 840 of the insertion device 810. The drive line assembly 840 of the insertion device 810 is composed of a drive mechanism 814 and a rod 825. Further, a manual axial force applied to an axial control assembly 830, in this embodiment comprising an outer cannula 811 and knob 813 of the insertion device, positions the band 310 along the axial length of the bobbin 800. By controlling the drive line assembly 840 and the axial control assembly 830 a user can create different shapes, such as conical, or "egg" shape, of the coiled band assembly 812.

The axial control assembly 830, e.g., outer cannula 811 and knob 813, may guide the drive line assembly (rod 812 and drive mechanism 814) and bobbin 800 into the vertebral body as well as move the band 310 axially over the bobbin 800. The knob 813 may be attached to a midsection of the outer cannula 811 in a fixed manner, such that the ends 817, 818 of the outer cannula 811 project past the knob 813. The knob 813 may have an opening 815 through which the band 310 is inserted through. The knob 813 may be cylindrical in shape as shown, or may have other shapes. The knob 813 may be made from different materials such as metal, plastic, and rubber. The outer cannula 811 has an inner diameter which is larger than the outer diameter of the rod 825, which may be inserted through the outer cannula 811. The distal end of the outer cannula 811 has attachment 816 which aids in guiding the band 310 onto the bobbin 800. The attachment 816 is preferably fixed to the outer cannula 811, but may also move, e.g., translate or rotate, relative to the outer cannula 811. The attachment 816, together with the manual axial force applied to the outer cannula 811, controls the position of the band 310 on the bobbin 800. Moving the attachment 816 axially back and forth causes the band 310 to move forward or rearward on the bobbin 800. The band 310 is coiled about the bobbin 800 underneath the attachment 816. The attachment 816 limits the diameter of the band mass about the bobbin 800. Although attachment 816 is shown have a curvature, preferably with a radius, other shapes are possible for attachment 816. The shape of attachment 816 can influence and limit the final shape of the coiled band assembly 812. While the axial control assembly has been described as comprising multiple pieces it can also comprise a single piece and is not limited to the form illustrated.

The drive line assembly 840 of the insertion device 810 may be comprised of the rod 825 and the drive mechanism 814. The rod 825 has a proximal end 819 and a distal end 820. At the proximal end 819, the rod 825 preferably has an attachment interface 822 that is compatible with the attachment interface 821 on the drive mechanism 814. One example of an attachment interface could be a ball detent mechanism such as those found on ratchet set drives, a bayonet nut connector, thread, conical connections, or hexagonal connector. A hex, star or other shaped male and female respective connectors may also be used. Other forms of interface attachments are contemplated. The distal end 820 of the rod 825 has another attachment interface 823 which is compatible with the attachment interface 824 on the bobbin 800 to preferably releasably attach the bobbin 800 to the rod 825. The drive mechanism 814 rotates the rod 825 about its longitudinal axis. The drive mechanism 814 may be hand driven, such as with a T-handle as depicted in FIG. 10, or mechanized, such as a motorized drill (not shown). Operation of the drive mechanism 814 causes the rod 825 to rotate, and the rod 825 causes the bobbin 800 to rotate. Alternatively, the drive mechanism 814 can be integral with the rod 825, or the drive mechanism preferably can releasably connect directly to the bobbin 800 such that rotation of drive line mechanism rotates the bobbin.

The bobbin 800 may comprise a cylindrical shaft, having a threaded exterior and whose outer diameter is smaller than the inside diameter of the outer cannula 811. The threaded exterior may aid in guiding the coiling band 310 about the bobbin 800. The bobbin 800 is attached to one end, the distal end, of the rod 825 and inserted through the outer cannula 811 such that the bobbin 800 projects from the distal end of the outer cannula 811. The bobbin 800 may also include a hole 801 through the cylindrical shaft so that an end of the band 310 may be fed through the hole 801 to preferably attach and hold the band 310 in place on the bobbin 800. Other means of attaching the band 310 to the bobbin 800 may be utilized.

Operation of the insertion device 810 and the bobbin 800 to create a final implant will now be discussed. The bobbin 800, having a band 310 inserted into the hole 801 of the cylindrical shaft is attached to the rod 825. The insertion device 810, comprising the drive line assembly 840 and the axial control assembly 830, with the attached bobbin 800 may be introduced into a collapsed vertebral body (not shown). The insertion device 810 is preferably inserted through a cannula but may be inserted through an open incision or percintaneous by piercing the skin and soft tissue with the bobbin 800 positioned in the vertebrae. The drive mechanism 814, connected to the rod 825, rotates the rod 825 such that the band 310 coils about the bobbin 800 to create a larger bobbiniband mass, also referred to as the final implant. The user may move the outer cannula 811 forward and backward, with respect to the collapsed vertebral body, to allow the band 310 to coil around the full axial length of the bobbin 800. Further, moving the outer cannula 811 forward and backward allows the user to create different shapes of the larger coiled band assembly. During coiling, the diameter of the coiled band assembly is increased to a desired size. The attachment 816 on the outer cannula 811 aids in creating different shapes of the larger coiled band assembly, as well as limiting the diameter of the coiled band assembly. The diameter of the implant can be varied along the length of the bobbin 800 to tailor the size and shape of the implant. Once the desired size and shape of the coiled band assembly has been achieved, the user cuts the band 310. This may occur outside the vertebral body. After the band 310 has been severed, the user rotates the rod 825 and bobbin 800 using the drive mechanism 814 to coil the end of the band about the bobbin 800, such that the band 310 is completely coiled about the bobbin 800 within the vertebral body. Once this is achieved, the user pulls on the rod 825 and drive mechanism 814, causing the rod 825 to detach from the bobbin 800, leaving the bobbin 800 in the vertebral body. The rod 825 may then be completely removed from the patient. Further, the outer cannula 811 is also removed after the rod 825 and bobbin 800 have been detached. PMMA or another cement or filler may be inserted into vertebral body containing the bobbin/band mass to further enhance fixation or repair of the damaged region.

Another embodiment of a bobbin implant is depicted in FIGS. 11-30. FIG. 11 depicts a bobbin 1160 with an insertion device 1000. Similar to the previous embodiment, the bobbin 1160 is rotated about its longitudinal axis and one or more bands 310 are coiled about the shaft of the bobbin 1160 to create a larger coiled band assembly. The insertion device 1000 transfers rotational motion from a drive mechanism (not shown) to rotate the bobbin 1160. When coiling a single band 310, the insertion device 1000 also preferably moves the band 310 axially along the shaft of the bobbin 1160. Whereas, when coiling multiple bands 310 about the bobbin 1160, no axial movement may be necessary. When various multiple bands 310 coil about the bobbin 1160, the bands 310 preferably coil about the bobbin 1160 at different locations along the shaft of the bobbin 1160. In a single band configuration, the insertion device 1000 preferably functions to rotate the bobbin 1160 about the bobbin's longitudinal axis, as well as provide axial movement of the band 310 with respect to the bobbin 1160. Rotation of the bobbin 1160 is accomplished through a drive line assembly 1300 comprising a drive shaft 1110, a flexible shaft 1070 and preferably a rotating a drive mechanism (not shown). While the drive line assembly 1300 is illustrated and described as comprising multiple pieces it may be a single component or comprise components other than those shown and described. Axial movement of the band 310 relative to the bobbin 1160, is accomplished through guide mechanism 1600 comprising a band guide conduit 1120, a spool holder 1030 and a cam disk 1010. While the guide mechanism 1600 is illustrated and described as comprising multiple pieces, it may also comprises a single component or additional components other than those shown and described. Moreover, while insertion device 1000 axially fixes the location of the bobbin 1160 and axially moves the band 310 along the axial length of the bobbin 1160, the position of the band 310 could be fixed and the bobbin 1160 could move axially.

Referring to the drive line assembly 1300, the drive shaft 1110 is generally cylindrical in shape and may have a length of about 115 mm, although other lengths are contemplated. A section 1116 of the drive shaft 1110, near the proximal end 1111, may have gear teeth about the circumference of the drive shaft 1110. The proximal end 1111 of the drive shaft 1110 extends from a proximal end 1023 of a housing 1020 of the insertion device 1000. As depicted in FIGS. 17A and B, the drive shaft 1110 proximal end 1111 has a quick coupling feature 1114 which is compatible with a drive mechanism, preferably a rotating drive mechanism that provides torque to drive shaft 1110, such as for example a T-handle or drill (not shown). A lock washer 1230 and stop disk 1170 are attached near the proximal end 1111 of the drive shaft 1110 (FIG. 12) preventing the drive shaft 1110 from moving in a distal direction. The lock washer 1230 and stop disk 1170 may abut an end cap 1100 (FIGS. 15A and B) attached to the proximal end 1023 of the housing 1020. The end cap 1100 is secured to the housing 1020 by shear stress pins 1260, preferably three shear stress pins 1260. Other means for securing the end cap 1100 to the housing 1020 may be used. The drive shaft 1110 projects through center hole 1102 in the end surface 1104 of the end cap 1100. The distal end 1112 of the drive shaft 1110 extends into the housing 1020 and has an attachment interface 1113 which may be compatible with an attachment interface 1075 on the proximal end 1074 of the flexible shaft 1070. One example of an attachment interface could be a ball detent mechanism such as those found on ratchet set drives, a bayonet nut connector, thread, or conical connections. Another example of an attachment interface could be a hexagonal or other shaped protrusion seating in a corresponding hexagonal or other shaped recess. The drive shaft 1110 connects to the flexible shaft 1070 in the interior of the housing 1020.

The flexible shaft 1070 (FIG. 26), connected to the drive shaft 1110 through attachment 1075 at its proximal end 1074, extends through a needle 1040. The flexible shaft 1070 preferably may comprise two components, a straight optionally rigid rod 1071 and a flexible component 1072 distal of the rigid rod 1071. The distal end 1073 of the flexible shaft 1070 connects to the bobbin 1160 preferably by a quick disconnect attachment 1076. The quick disconnect attachment 1076 may take any number of forms, such as a ball detent mechanism such as those found on ratchet set drives, a bayonet nut connector, thread, conical connections, hexagonal connector, etc. The attachment 1076 also allows the flexible shaft 1070 to disconnect from the bobbin 1160 when a user pulls the drive shaft 1110 together with the flexible shaft 1070 in a proximal direction along the longitudinal axis of the housing 1020 and drive shaft 1110. A drive mechanism rotates the drive shaft 1110 which in turn rotates the flexible shaft 1070 which rotates the bobbin 1160. The flexible shaft 1070 rotates within main bore 1042 formed in the needle 1040.

Figure 23A:
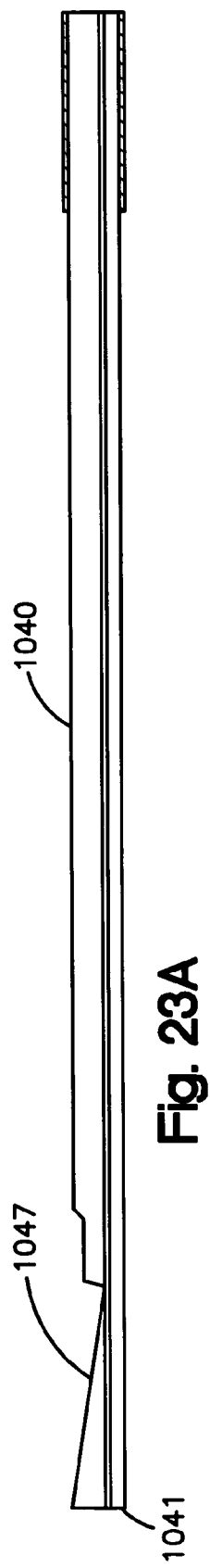
FIGS. 23A and B is a cross-sectional view and an end view, respectively of an embodiment of a needle of the present invention.
Figure 23B:
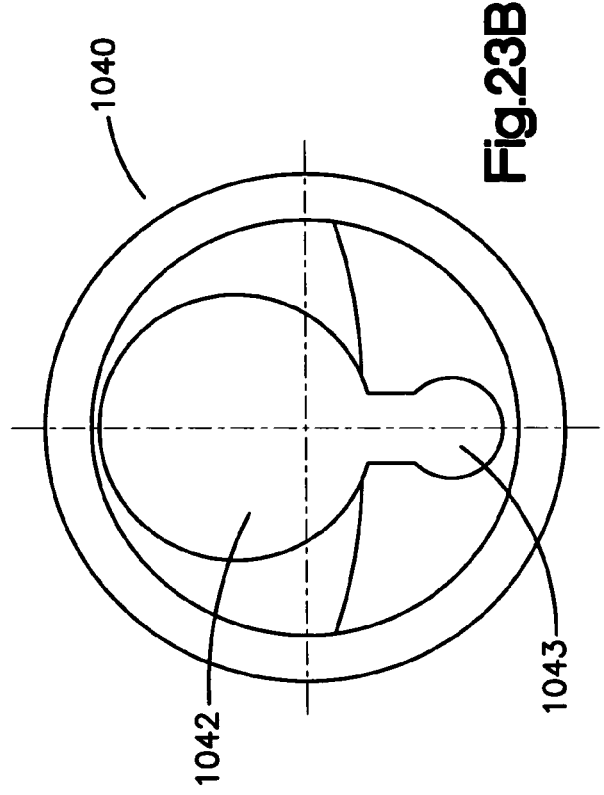

The needle 1040 assists in inserting the bobbin into the vertebral body, similar to the outer cannula 811 of the previous embodiment. The needle 1040 (FIGS. 22-24) is preferably fixed to and extends from the distal end 1026 of the housing 1020. The needle 1040, in particular the configuration of the distal end 1041 of the needle 1040, can take various shapes and forms some of which are illustrated in FIGS. 22-24. The needle 1040 is generally cylindrical in shape with a half cylinder shape at its distal end 1041. The needle 1040 may have a length of about 126 mm with an outside diameter of about 5 mm, although these length and diameter are only exemplary and other lengths and diameters are contemplated. The distal end 1041 may have a flat, open surface 1047 on which the bobbin 1160 rests. In the alternative, the flat surface 1047 may be inclined such that the distal end 1041 has a larger dimension, causing the flexible shaft 1070 to bend (FIG. 23A). A threaded pin 1270 through the hole 1022 at a distal end 1026 of the housing 1020 holds the needle 1040 to the housing. Other means of fixing the needle 1040 to the housing are contemplated.

Figure 12:
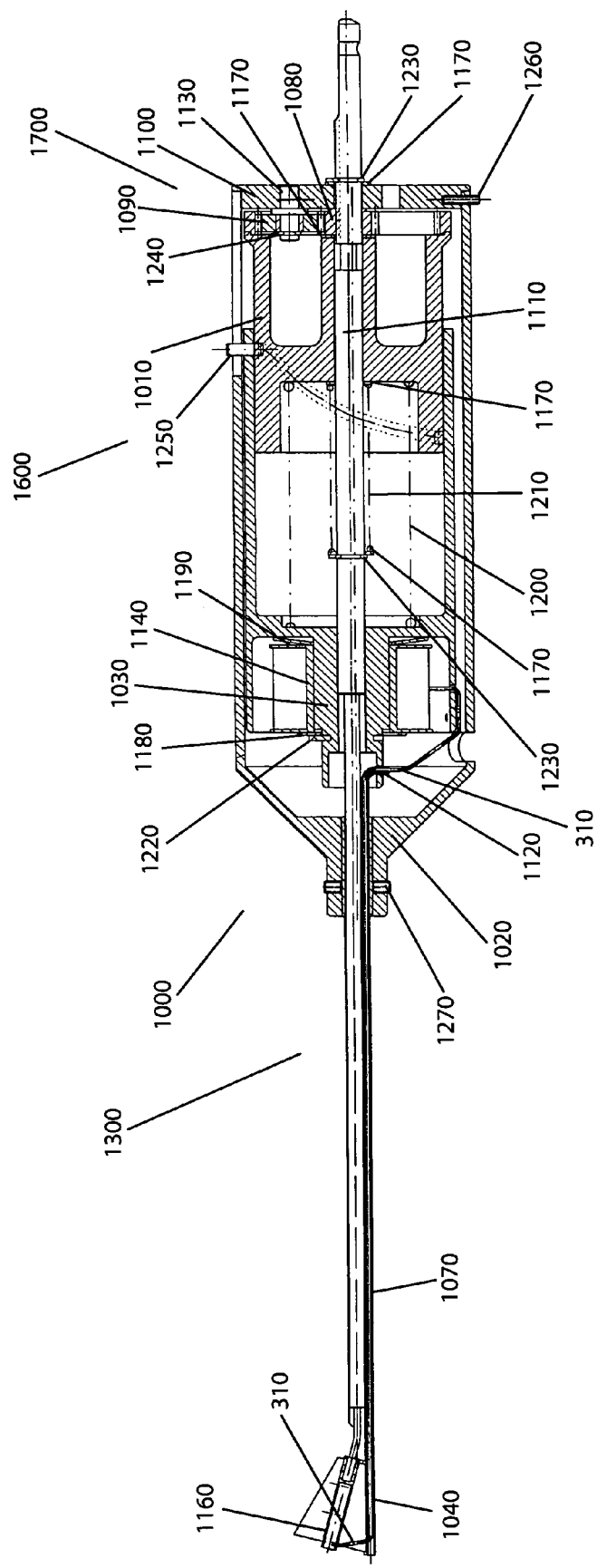
FIG. 12 is a cross-sectional view of the insertion device and bobbin depicted in FIG. 11.
Figure 13:
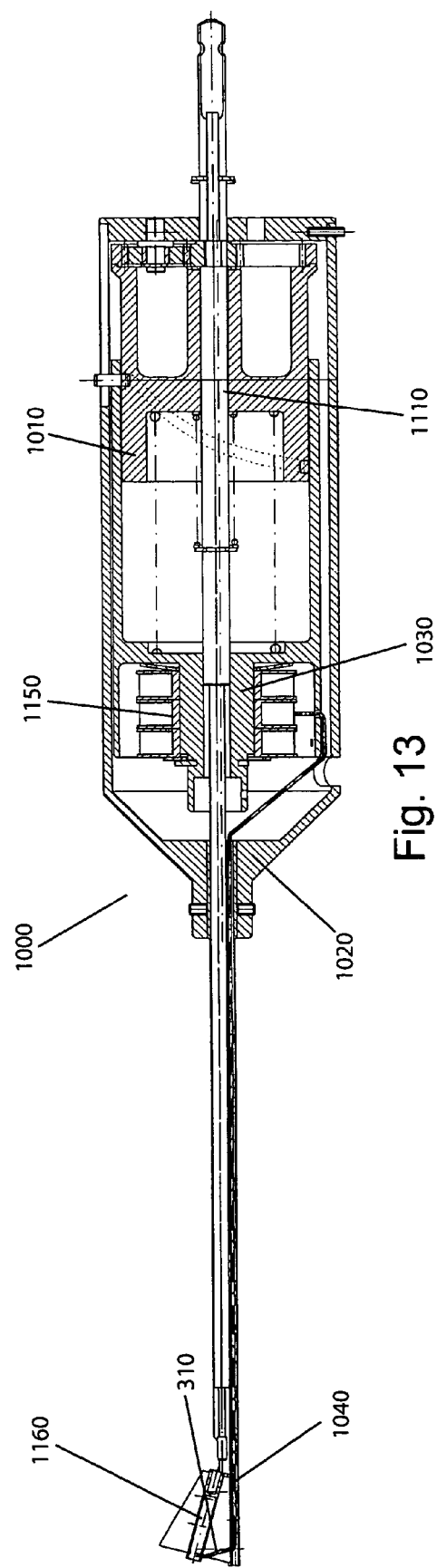
FIG. 13 is cross-sectional view of the insertion device and bobbin of FIG. 11 depicting the use of small band spools.

The bobbin 1160 (FIGS. 27A-C) may be cylindrical, having a length of about 16 mm and a diameter of about 2.5 mm, although this length and diameter are merely exemplary and other lengths and diameters are contemplated which would depend, in part, upon the desired final implant shape. The bobbin 1160 may have a rough surface providing friction to the surrounding band so as to ease force transfer between the rotating bobbin 1160 and the coiled band 310 The proximal end 1061 includes a quick disconnect attachment 1062 complementing the attachment 1076 on the flexible shaft 1070. The distal end 1163 of the bobbin 1160 may be hollow. At the distal most end of the bobbin 1160 a hole 1164 may extend through the diameter of the bobbin 1160. Two additional holes 1165, 1166 may be included. These holes extend only through one side of the outer circumference of the bobbin 1160. The holes 1164, 1165, and 1166 may assist in attaching the band 310 to the bobbin 1160. With the band 310 attached to the bobbin 1160, rotation of the bobbin 1160 will cause the band 310 to wrap around the bobbin 1160. Rotational motion of the bobbin 310 pulls the band 310 from band spools 1140, 1150 located inside the housing 1020. The cone shape about the bobbin 1160 in FIGS. 11 and 12 depicts one exemplary shape the coiled bobbin may form when implanted in a vertebrae.

Axial movement of the band 310 relative to the bobbin 1160 is accomplished through guide mechanism 1600 comprising the band guide conduit 1120 (FIG. 25), spool holder 1030, cam disk 1010, and a gear train 1700. In the insertion device 1000 the rotary motion of the drive mechanism is converted to an axial motion which is transferred to the band guide conduit 1120 to control the axial location where the and 310 is coiled onto the bobbin 1160. The gear train 1700 may comprise drive gear 1080 and sprocket 1130 on which gear 1090 is mounted. The gear train 1700 functions to transfer the rotational force of the drive shaft 1110 to the cam disk 1010, such that the cam disk 1010 may rotate at a different speed than the drive shaft 1110, for example the cam disk 1010 preferably may rotate once for every five rotations of the drive shaft 1110. The cam disk 1010 converts the rotational force of the drive shaft 1110 to an axial, preferably oscillating force due to cause the spool holder 1030 to move axially, preferably oscillate back and forth. The spool holder 1030 moves the band guide conduit 1120 similarly in an axial direction, preferably in an oscillating back and forth motion. The purpose of the axial movement is to have the band 310 move axially, relative to the bobbin 1160.

More specifically, the teeth of drive gear 1080 meshes with the teeth 1116 of the drive shaft 1110 and with the teeth of gear 1090, which rotates about sprocket 1130. The teeth of gear 1090 also meshes with teeth 1016 located at the proximal end 1017 of the cam disk 1010. That is, the drive gear 1080 interacts with both the drive shaft 1110 (FIGS. 17A and B) and the gear 1090, causing the cam disk 1010 to rotate at a different speed, preferably slower speed, than the drive shaft 1110. Gear 1090 is seated over sprocket 1130 (FIG. 16) which is held in place by a lock washer 1240. The gear train 1700 can be configured to cause the cam drive at the desired speed to control the axial motion and depending upon the gearing, cam disk 1010 can rotate faster or slower than the drive shaft 1110.

The cam disk 1010 (FIG. 18) is cylindrical in shape having a length of about 41 mm and an external diameter of about 31.5 mm, which is smaller than an inner diameter of the housing 1020. Other sizes, lengths and diameters can be utilized for the cam disk 1010. The cam disk 1010 is structured with a cross member 1011 and center core 1012 having an inner passage 1013 allowing the drive shaft 1110 to pass through the center of the cam disk 1010. The inner passage 1013 helps maintain alignment of the drive shaft 1110. The drive shaft 1110 is free to rotate in inner passage 1013 relative to the cam disk 1010. The external diameter of the cam disk 1010 has a groove 1014 about its circumference.

The spool holder 1030 (FIGS. 19A and B) is also cylindrical in shape, having a distal end 1037 and a proximal end 1034. The outer diameter of the spool holder 1030 is smaller than the inner diameter of the housing 1020, but larger than the distal end of the cam disk 1110. Similar to the cam disk 1010, the spool holder 1030 has a cross member 1031 and center core 1032 having an inner passage 1033. The drive shaft 110 and flexible shaft 1070 are free to rotate in inner passage 1033 relative to spool holder 1030. The proximal end 1034 of the spool holder 1030 has a cavity 1037 which receives the distal end 1015 of the cam disk 1010 such that the proximal end 1034 of the spool holder 1030 overlaps the cam disk 1010 and is between the housing 1020 and the cam disk 1010. The overlap is sufficiently large so that as the spool holder 1030 moves towards the distal end 1026 of the housing 1020 (discussed later) the proximal end 1034 of the spool holder 1030 continues to overlap the distal end 1015 of the cam disk 1010.

The spool holder 1030 is prevented from rotating about its longitudinal axis within the housing 1020 by dowel pin 1250 extending through hole 1035 in the proximal end 1034 of the spool holder 1030. The dowel pin 1250 extends into the groove 1014 of the cam disk 1010 and through slot 1024 at the proximal end 1023 of the housing 1020. The gear train 1700 rotates the cam disk 1010 and as the cam disk 1010 rotates, dowel pin 1250 moves along slot 1024 due to the inclination of the groove 1014 in the cam disk 1010. As the dowel pin 1250 moves axially along slot 1024 it moves spool holder 1030 axially as well. Thus, the spool holder 1030 undergoes the same motion as the dowel pin 1250 and provides a visual indicator of the location of the spool holder and the position of the band 310. If the dowel pin 1250 moves back and forth in slot 1024 then the spool holder 1030 will likewise move axially back and forth.

Either a large band spool 1140 (FIGS. 20A and B) or a small band spool 1150 (FIGS. 21A and B) or multiple band spools can be placed over the center core 1032 of the spool holder 1030. The band spool 1140, 1150 may be held in place by a displacement disk 1180 and lock washer 1220. Between the band spool 1140, 1150 and the cross member 1031 of the spool holder 1030 a spring 1190, such as leaf spring, maintains the band spool 1140, 1150 against the displacement disk 1180. As the bobbin 1160 rotates, it unspools the band 310 from the band spool 1140, 1150. A pressure spring 1200, such as a helical spring, is located between the cam disk 1010 and the spool holder 1030, coaxial with the drive shaft 1110. The pressure spring 1200 maintains tension on the band, so as the spool holder 1030 moves axially backward, the band 310 does not get entangled. The pressure spring 1200 also aids in maintaining the components in place.

The band 310 from the band spool 1140, 1150 passes through hole 1038 in the spool holder 1030 and is inserted into the interior conduit 1123 at the proximal end 1121 of band guide conduit 1120. The band guide conduit 1120 is located in groove 1043 of the needle 1040. The proximal end 1121 of the band guide conduit 1120 is attached to the spool holder 1030 through a hole 1036 at the distal end 1037 of the spool holder 1030. Thus, as the spool holder 1030 moves axially within the housing 1020, the band guide conduit 1120 moves similarly, preferably axially back and forth in the needle 1040. The distal end 1122 of the band guide conduit 1120 terminates in the groove 1043 of the distal end 1041 of the needle 1040. The band guide conduit 1120 moves axially relative to the bobbin 1160, thus controlling the position along the axial length of the bobbin 1160 where band 310 is placed.

Attached to the drive shaft 1110 between the spool holder 1030 and cam disk 1010, is a second stop disk 1170 and a lock washer 1230. Connected to the second stop disk 1170 and the cam disk 1010 is a pressure spring 1210. This pressure spring 1210, similar to pressure spring 1200 aids in keeping the components in a defined position.

The housing 1020 (FIGS. 14A and B) is cylindrical in shape having a proximal end 1023 and a distal end 1026, and houses the above described components. The diameter of the housing 1020 at the distal end 1026 tapers at approximately 45 degrees to a smaller diameter forming a nozzle 1021. Other shapes and sizes for the housing are contemplated. Another slot 1025, perpendicular to the housing's longitudinal axis is located near the distal end 1026 of the housing 1020. This slot 1025 provides access to band(s) 310 proximate the band spool 1140, 1150 to allow a user to cut the band(s) 310 once the bobbiniband mass has obtained its desired size.

In a multiple band configuration of the insertion device 1000 (FIG. 28), a band guide conduit 1120, a cam disk 1010 preferably may not be employed. No axial movement may be required when coiling multiple bands 310 about the bobbin 1160, however, if desired axial movement may be provided. One reason that axial movement may be unnecessary is that each band 310, passing through holes 1038, 1039, and 1191 in the spool holder 1030 and through bores 1044, 1045, and 1046 of needle 1040, are attached to the bobbin 1160 at a different location along the shaft of the bobbin 1160, through holes 1164-1166. In the multi-band embodiment, bands of different sizes, thickness and shapes may be utilized to configure the final implant shape. Preferably, the thickest band coils about the distal end 1163 of the bobbin 1160, with success thinner bands coiling next to the previous band 310. Thus, as the bobbin 1160 rotates, multiple bands 310 coil about the bobbin. And as the bobbin 1160 rotates more, the bands will naturally spread out along the shaft of the bobbin, creating a coiled band assembly. Thus, in a multiple band configuration, the insertion device 1000 may function to rotate the bobbin 1160 about the bobbin's longitudinal axis with little or no axial movement about the insertion device's longitudinal axis to the band 310 with respect to the bobbin 1160. Accordingly, the internal components of the housing 1020 may not need to move axially in a multiple thread configuration. Similarly, the cam disk 1010 does not rotate either.

To disengage the axial guide mechanism 1600, the drive shaft 1110 is displaced in a proximal direction until a narrower section 1115 of the drive shaft corresponds with the location of drive gear 1080. Because this section 1115 of the drive shaft is narrower and has no gear teeth, the gear teeth of drive gear 1080 not do interact with the drive shaft 1110. Accordingly, as the drive shaft 1110 rotates, there is no corresponding interface between the drive shaft 1110 and the gear train 1700. Thus, the gear train 1700 does not rotate, and therefore no rotational force is applied to the cam disk 1010. Because the cam disk 1010 does not rotate, the spool holder 1030 does not move axially.

The needle 1040 (FIGS. 24A-C) may include three additional bores 1044, 1045, 1046 instead of the groove 1043. Each additional bore allows for a band 310 to be threaded through. The additional bores may have different diameters to accommodate different sizes of the band. Where no axial movement of the guide mechanism 1600 is required, the band guide conduit 1120 may be unnecessary and the bands may be inserted directly through bores 1044, 1045, and 1046 as shown in FIG. 28.

The operation of the bobbin 1160 and insertion device 1000 will now be described. A band spool 1140, 1150 containing a band 310 is secured to the spool holder 1030 inside the housing 1020. The band 310 is threaded from the band spool 1140, 1150 through hole 1038 in the spool holder 1030 and through the band guide conduit 1120 along the needle 1040 such that the band 310 exits the needle 1040 at its distal end 1041 and is attached to the bobbin 1160 through one of the holes 1064, 1065, and 1066 of the bobbin 1160. Other means may be used to attach the band 310 to the bobbin 1160. The bobbin 1160 with the band 310, together with the needle 1040, is inserted into the collapsed vertebral body, for example either down a cannula or an open surgical field.

The user rotates a drive mechanism causing the drive shaft 1110 to rotate. This rotation causes the cam disk 1010 and flexible shaft 1070 to rotate. The dowel pin 1250 seated in the groove 1014 of the cam disk 1010 causes the spool holder 1030 to move axially forward and back, depending on the shape of the groove 1014. The axial movement of the spool holder 1030 is transferred to the band guide conduit 1120, causing the band guide conduit 1120 to move axially in needle 1040. This axial movement determines the location where the band 310 is coiled about the bobbin 1160. Meanwhile, the rotation of the flexible shaft 1070 causes the bobbin 1160 to rotate which causes the band 310 to uncoil from the spool 1140, 1150 and be fed through the band guide conduit 1120 and wrap around the bobbin 1160. When the bobbin 1160 has obtained the desired mass and shape, the user stops rotation of the drive shaft 1110 and cuts the band 310 through the perpendicular slot 1025 in the housing 1020. The user then rotates the drive shaft 1110 so that the band 310 remaining in the band guide conduit 1120 is coiled about the bobbin 1160. Once completed, the user pulls on the drive shaft 1110, disconnecting the bobbin 1160 from the flexible shaft 1070, leaving the bobbin 1160 in the vertebral body. The user then removes the needle 1040 from the vertebral body. Alternatively, the user can pull on the housing 1020 simultaneously disconnecting the bobbin 1160 from the flexible shaft 1070 and removing the insertion device 1000 from the patient. PMMA or another cement or filler may be inserted into vertebral body along with bobbin to further enhance fixation or repair of the damaged region. Alternatively, the band 310 may be coated with or contain bone cement or other material that may be activated after or during insertion of the bobbin, coiled body.

Figure 28:
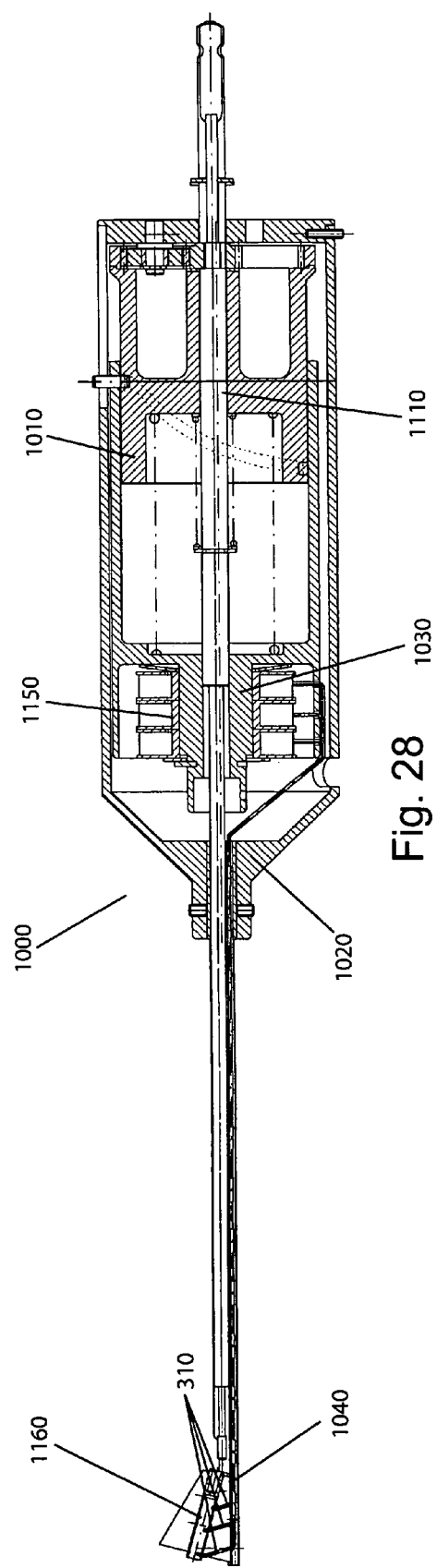
FIG. 28 is a cross-sectional top view of another embodiment an insertion tool and bobbin of the present invention, depicting three bands.

As discussed previously, multiple threads, of varying diameter may be coiled onto the bobbin to create the final implant (FIG. 28). This requires multiple band spools to be inserted into the housing 1020 of the insertion device 1000. The bands from these spools are threaded through the bores 1044, 1045, and 1046 of needle 1040 depicted in FIGS. 24A-C. Preferably no band guide conduit 1120 is employed in a multiple band configuration (although one or more band guide conduits may be utilized), and the flexible shaft 1070 and bobbin 1160 preferably do not move axially. Preferably the largest band is inserted in bore 1045 such that it exits at the most distal end of the needle 1040. The next largest band is preferably inserted in bore 1044, such that it exits needle 1040 proximal to bore 1045, as shown in FIG. 24B.

Prior to performing a procedure, a user may be provided with a number of insertion devices for implanting a bobbin 1160. Each insertion device may have a different cam disk having a different groove configuration. As discussed previously, the groove configuration in part determines the shape of the bobbin. In addition, each insertion device may include different band configurations or sizes. Thus, user can chose the best insertion device to provide the desired coiled band assembly configuration.

In the alternative, a user may remove the end cap 1100 to gain access to the inner components of the housing 1020. In this manner, the user can exchange cam disks 1010 and add spools of band after the existing spool of band is exhausted. Once the proper configuration of cam disk 1010 and size(s) of band is inserted into the housing, the user re-attaches the end cap 1100, securing it with the shear stress pins 1260. Other means of accessing the internal component of the insertion device, such as quick release mechanism may also be used. The insertion device may be configured for single or multiple uses. For example, a single use device may be made of plastic and may be made such that it cannot be reused. For example, the plastic housing could be molded so that the spool of band material can not be replaced without breaking the housing, or such that the band material can not be re-threaded in the band guide conduit/needle once the band has been cut and coiled onto the bobbin. Alternatively, or in addition to, the connection between the bobbin and the flexible shaft could be damaged when the bobbin is disengaged from the flexible shaft such that a new bobbin will not mate or attach to the flexible shaft. If the insertion device is configured to be reusable consideration should be made to sterilize the device for the next use which may require different materials than single use applications.

Figure 29:
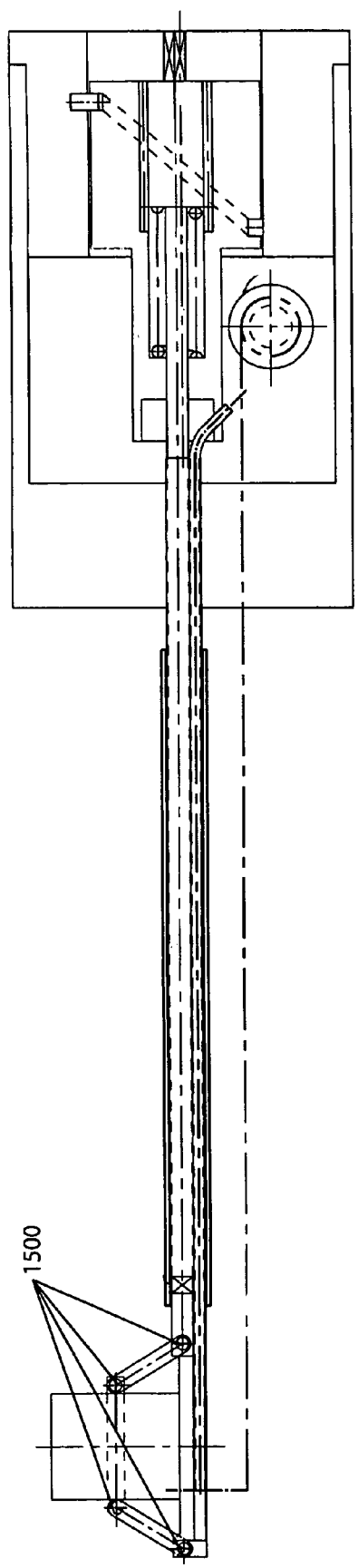
FIG. 29 is a cross-sectional view of the present device depicting the flexible shaft having four joints.
Figure 30:
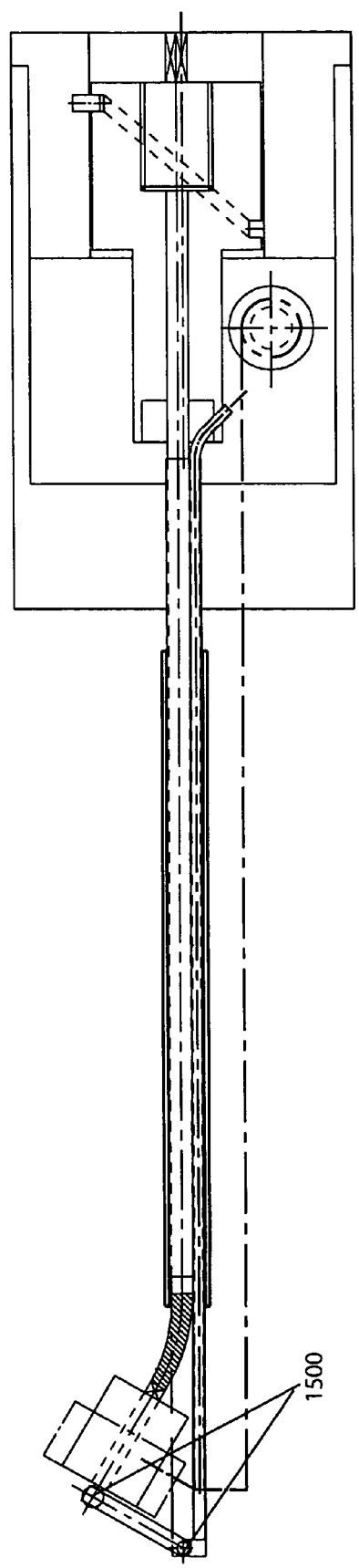
FIG. 30 is a cross-sectional view of the present device depicting the flexible shaft having two joints.

FIG. 29 illustrates the use of a flexible shaft having four joints 1500. The joints 1500 may be in the form of universal joints. This configuration of the flexible shaft 1070 allows the bobbin to remain parallel with the needle 1040. FIG. 30 illustrates the use of a flexible shaft having two universal joints 1500. This configuration allows the flexible shaft to support the bobbin at a predetermined angle.

In some embodiments, band 310 may be wound inside a bendable sheet 2000, such as a sheet of metal, plastic, Teflon or other material, wrapped around a bobbin. For example, FIG. 31A shows a transverse cross sectional view taken across an end of a bobbin, e.g., bobbin 600, having a sheet 2000 wrapped around bobbin 600 before winding of band 310. Referring to FIG. 31B, as band 310 is wound around bobbin 600, sheet 2000 expands as coil 612 increases in diameter. Such expansion can force sheet 2000 outward, for example against structures within vertebral body 12. In other embodiments, an expandable or elastic bag, balloon, or other structure, which may or may not have a predefined shape, can be used instead of or in addition to sheet 2000 around coil 612 which can expand within vertebral body 12 as the coil increases in size.

Referring to FIG. 32, a bobbin 2100 may be bendable instead of or in addition to having joints as described above. Such a bendable bobbin 2100 may help optimize repositioning and augmentation of damaged bone by conforming within vertebral body 12 and applying a stabilizing force against inner walls of the vertebral body 12. Such bendable bobbins may be comprised of various materials, such as polymers, metals, biomaterials, or any other compatible materials.

As mentioned above, a variety of types of bobbins having various geometries and other features and characteristics may be used. For example, the bobbin may be straight bobbin 300 or a curve bobbin such as bobbin 2100, and may comprise a variety of materials. In other embodiments, a bobbin 600 can have joints such as joints 614 and 616 to allow movement of each portion 601, 603, and 620 to provide a desired orientation and configuration of bobbin 600 within a vertebral body or other structure to be repaired, distracted, or otherwise manipulated.

Figure 34B:
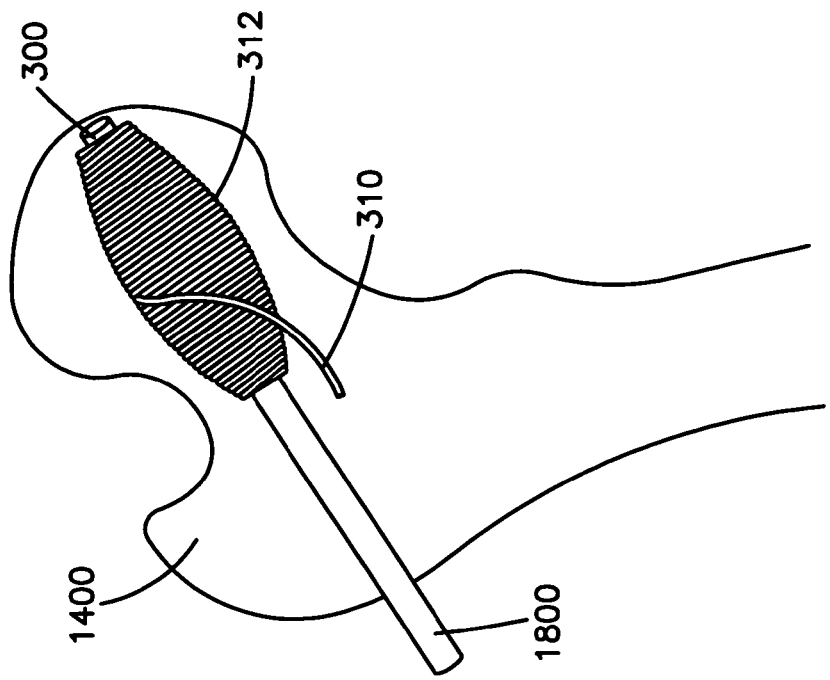
FIGS. 34A and B are cross sectional views of an expandable osteopathic augmentation apparatus in use in a proximal femur according to an embodiment of the present invention.
Figure 34A:
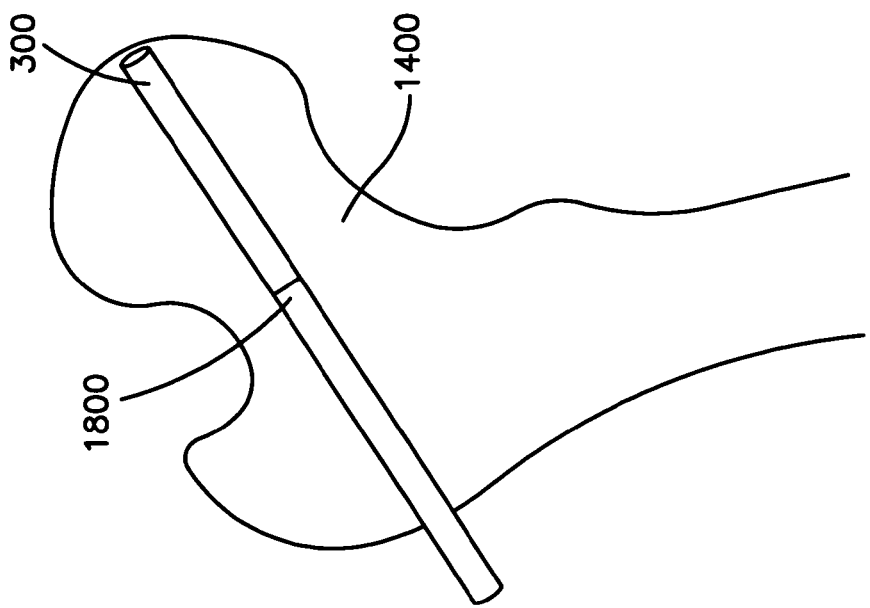

Although the apparatus and methods described herein thus far have been described in the context of repositioning and augmenting vertebral bodies following vertebral compression fractures, various other uses and methods are envisioned. For example, in some embodiments, a bobbin such as bobbin 300 and band 310 may be used to reposition and/or augment other damaged bone regions such as a fractured or weak proximal femur 1400 as shown in FIGS. 34A and B. In such embodiments, bobbin 300 may be inserted through a cannula, and may include an extension 1800 to which it is releasably connected. bobbin 300 may have various features as described elsewhere herein. After band 310 is coiled about the bobbin, the coiled band body 312 may be detached from the extension and left in position in the femur. The cavity left by the extension and the volume surrounding the coiled band body may be filled with bone cement, bone chips, or other material to integrate the coiled band body into the bone.

In another embodiment, the implants may be, for example, wool bales or fibrous masses/bodies comprising a shape memory metal or metal alloy (e.g., a nickel titanium alloy such as nitinol) or another material that may or may not have shape memory characteristics. The fibrous masses may have any desired shape, e.g., cylindrical, spherical, or another shape (e.g., see FIG. 35).

In some embodiments, the wool bales or fibrous masses/bodies (generally referred to herein as "fibrous masses") may comprise a continuous or segmented thread, wire, strand or other elongated member (generally referred to herein as a "fiber"). The one or more fibrous masses may be comprised of any biocompatible material having desired characteristics of shape memory, flexibility, strength, and/or other characteristics. For example, in some embodiments the fibrous masses may be comprised of a fiber, wire, thread or other relatively thin structure of a biocompatible shape memory alloy, stainless steel, titanium, polymer, tricalcium phosphate, or any other material having desired characteristics. In some embodiments, the fibrous bodies may be resorbable.

As shown in FIGS. 36A and B, fibrous masses comprising a shape memory alloy (e.g., nitinol) may expand when the fibrous mass is heated to a temperature over an actuation temperature, for example as the shape memory alloy undergoes a phase transformation between a Martensite state (e.g., at a low temperature) and an Austenite state (e.g., at a higher temperature). The actuation temperature of shape-memory alloy fibers within the wool bales may be, for example, between about 28° C. and about 36° C. Alternatively, a fibrous mass may expand, contract, or otherwise change shape or configuration when it is activated by an energy source (e.g., an ultraviolet light, ultrasonic radiation, radio waves, heat, electric or magnetic field).

The wool bales or fibrous masses may have an initial diameter that is small enough to allow one or more bodies to be inserted into a vertebral body or other bone thorough a cannula or other introducer as shown in FIG. 37. For example, the wool bales 4000 may have an initial diameter that is between about 1 mm and about 10 mm. Other sizes may be used.

As shown in FIG. 37, a minimally invasive method of augmenting a damaged vertebral body 12, e.g., following a vertebral compression fracture, may comprise implanting one or more wool bales or fibrous massesibodies into an inner portion of a vertebral body between the upper and lower endplates of the vertebral body. An access may be formed in the outer cortical shell of vertebral body by a trocar, drill or other instrument. The wool bales or fibrous masses/bodies may then be implanted, for example, through a cannula 4100 or introducer inserted into vertebral body as shown in FIG. 37. Suitable procedures and materials for inserting a cannula through which the masses may be introduced are known in the art, and may be similar to those described above for kyphoplasty and other procedures. For example, the cannula 4100 may be introduced using a posterior approach as shown in FIG. 2, e.g., through a pedicle and into the interior of the vertebral body.

The fibrous masses 4000 may be sized to be inserted into the vertebral body 12 through the cannula 4100 and may expand after being implanted in the vertebral body 12 to compact or compress the bone material inside the vertebral body. Alternatively, after the passageway is formed in the vertebral body, instruments such as, for example, currettes or balloon catheter may be used to compress and compact the bone inside the vertebral body to create a cavity. The cavity in the vertebral body also may be formed by removing bone material as opposed to compacting the bone. For example, a reamer or other apparatus could be used to remove bone material from the inside of the vertebral body.

Figure 38:
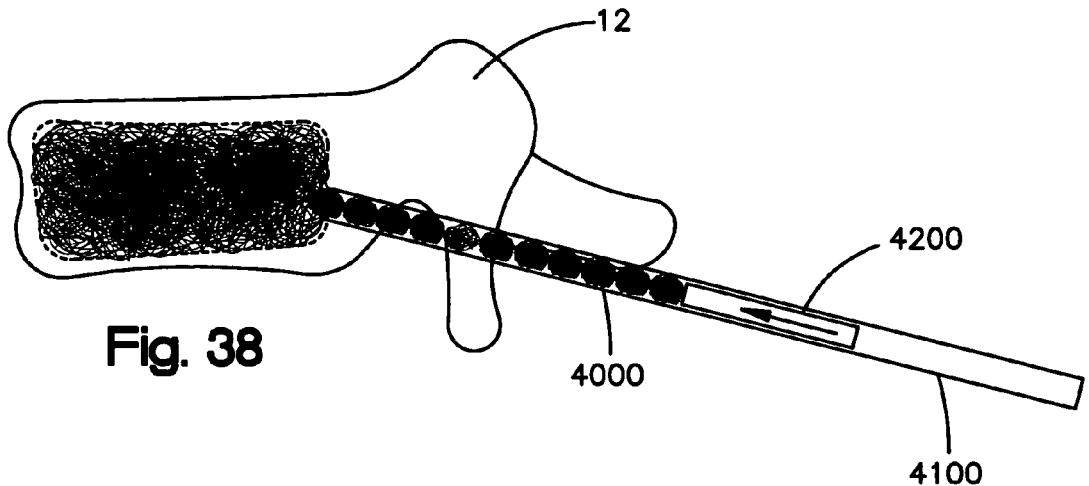
FIG. 38 is an illustration depicting fibrous masses expanded after insertion into the vertebral body.

As shown in FIGS. 37 and 38, the fibrous masses may be inserted through the cannula and into the central portion of the vertebral body using a displacement device 4200 or other apparatus. For example, a plunger, pusher or other displacement member inserted within the cannula 4100 may be used to displace or push the fibrous masses 4000 through the cannula 4100 and into the vertebral body 12. The displacement device 4200 may be driven, for example, by pressure, e.g., from a syringe, rod, or other apparatus that forces the displacement device 4200 into the cannula 4100 and towards the vertebral body 12.

When the fibrous masses 4000 are inside the vertebral body, they may be heated, for example by the body temperature of the patient, to a temperature that is over the actuation temperature (e.g., about 28° C. to about 36° C.). At the actuation temperature, the fibrous masses may expand as shown in FIG. 38. The expanded fibrous masses may help restore the height of the vertebral body, and may help restore lordosis of the spine.

Figure 39:
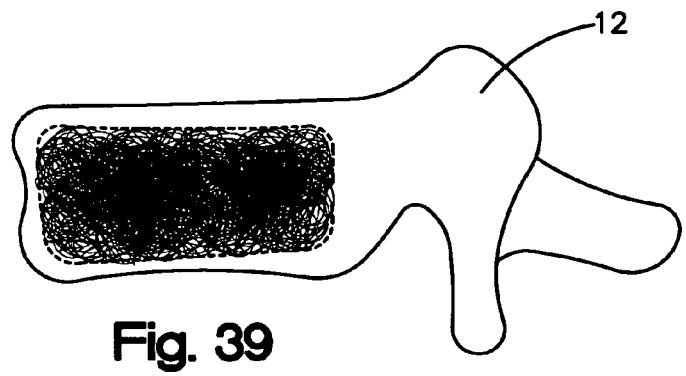
FIG. 39 is an illustration depicting expanded fibrous masses in the vertebral body.

As shown in FIG. 39, as more fibrous bodies are inserted into the vertebral body, and/or as the fibrous masses are expanded, they may fill a central portion of vertebral body and can push against the inner sides of the endplates of the vertebral body. Outward forces imparted by the fibrous masses within the vertebral body may spread the endplates apart and tend to restore vertebral body toward its original height, and may provide structural support to stabilize the vertebral body.

Insertion and expansion of the fibrous masses into a vertebral body may also compact the cancellous and osteoporotic bone inside the collapsed vertebral body. Any desired number of fibrous masses may be inserted, and each fibrous mass may have a desired configuration in order to augment the bone.

Figure 40:
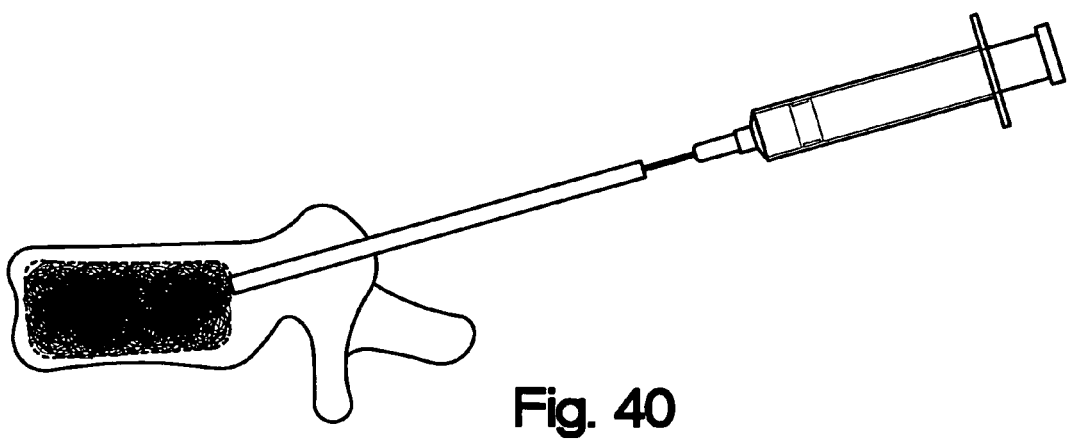
FIG. 40 is an illustration depicting a vertebral body being filled with bone cement or other bone filler material.

As shown in FIG. 40, after insertion of one or more wool bales 4000 or other fibrous masses/bodies, a bone cement (e.g., PMMA or tricalcium phosphate), bone chips, demineralized bone, or other bone filler or implant may be inserted to further augment or stabilize the vertebral body.

After injection or insertion of the filler material, the cannula or other introducer may be removed. As shown in FIG. 41, the fibrous masses within the vertebral body may help limit or prevent leakage of the cement or other filler, and may increase the shear strength of the bone cement or filler material.

In some embodiments a pedicle screw, a chain, or other elongated member may attach to and/or extend from the vertebral body to provide a tensioning member to reposition the vertebral body, for example as described in U.S. Provisional Patent Application No. 60/722,064, entitled "Apparatus and Method for Vertebral Augmentation using linked bodies", filed Sep. 28, 2005, which is incorporated by reference herein in its entirety.

The fibrous masses may be of a uniform or non-uniform size, shape and materials. One or more fibrous masses may be implanted into a bone or other cavity individually or linked together in a desired configuration. As shown in FIGS. 42 and 43, fibrous bodies described herein may have any desired geometry, configuration and/or shape memory characteristics.

For example, as shown in FIG. 42, an implant of fibrous bodies may comprise substantially spherical fibrous bodies which may be joined by and/or threaded upon one or more other fibers. In other embodiments a chain may have different configurations of fibrous bodies that may or may not be joined.

As shown in FIGS. 43A-D, different configurations of wool bales or fibrous masses/bodies may be used. For example, the fibrous masses may be configured as substantially spherical, ellipsoidal, cylindrical, or any other shape or dimension that may fit through a cannula or other introducer. A fibrous mass may also have a different size, shape or configuration after activation or expansion, for example as shown in FIGS. 43A-D.

One or more fibrous masses may be inserted, possibly with one or more other implants, and may become tangled and/or convoluted with the other fibrous bodies or implants within the vertebral body. For example, after insertion, the fibrous masses may become further attached together and/or tangled such that that the masses become a larger mass filling the spaces within the vertebral body. Such larger mass may lock into the vertebral body and resist removal through the insertion opening. In some embodiments, one or more fibrous masses or other implants may be coated with an adhesive, such that the implant may inserted into vertebral body in a substantially flexible state and may become more rigid and/or tangled or convoluted during or after insertion.

Figure 44C:
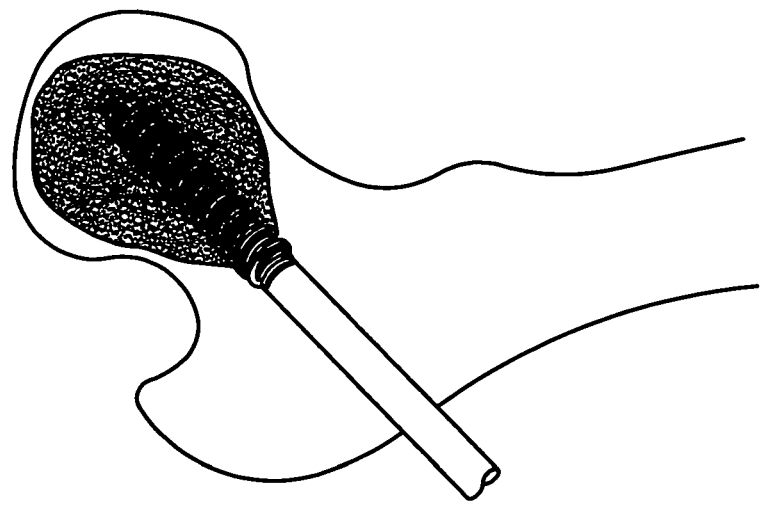
FIGS. 44A-C are illustrations depicting wool bales or fibrous masses/bodies of the present invention augmenting other bones, e.g. a proximal femur.
Figure 44B:
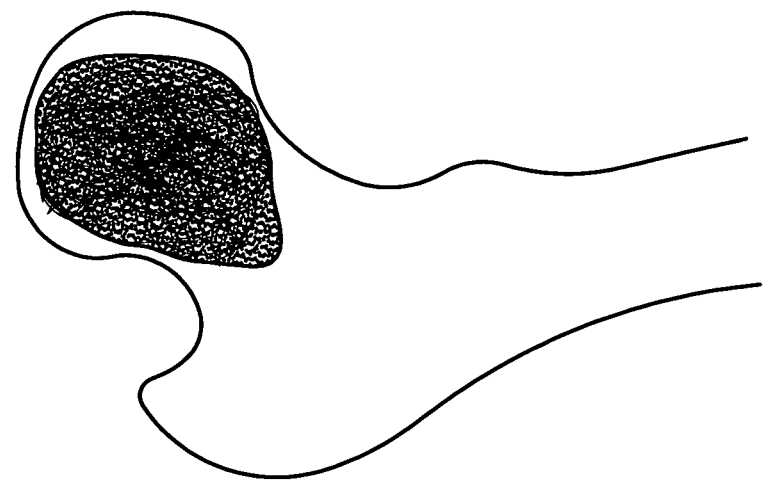
Figure 44A:
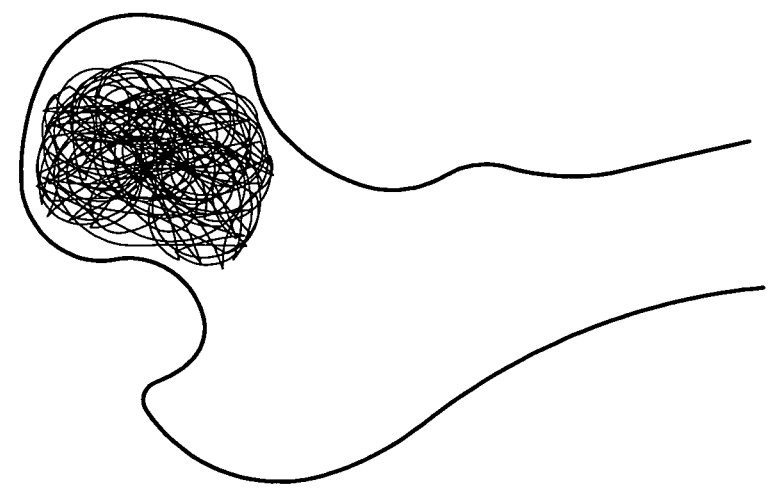

Although the apparatus and methods described herein thus far have been described in the context of repositioning and augmenting vertebrae in the context of vertebral compression fractures and deformations in spinal curvature, various other uses and methods are envisioned. For example, in some embodiments, one or more implants comprising fibrous masses may be used to reposition and/or augment other damaged bone regions such as a fractured or weak proximal femur as shown in FIG. 44A-C.

In such embodiments, for example, one or more fibrous masses or chains of fibrous masses may be inserted into a head of a femur, e.g., through a cannula or other introducer. Once inserted, the fibrous mass may compact material within the head of the femur and provide solid support to augment the head. In some embodiments, the fibrous mass may comprise a shape memory alloy and expand or otherwise change its configuration after insertion (e.g., after heating to a temperature above an activation temperature). A bone cement or other filler may also be used to aid augmentation. In other embodiments, for example as shown in FIG. 44C, another implant such as a screw or other device may be inserted in addition to or instead of one or more fibrous masses.

In some embodiments, the implants and methods described herein may be used in conjunction with other apparatus and methods to restore lordosis and augment a vertebral body. For example, one or more fibrous mass implants or coiled bodies may be used in conjunction with known procedures, e.g., a balloon kyphoplasty, which may be used to begin repositioning of a vertebral body and/or create a space within the body for the implant. In other embodiments, one or more implants described herein may be used in conjunction with other tools or devices, e.g., an external fixation apparatus for helping to manipulate or fix the vertebrae or other bones in a desired position.

In another embodiment, a kit may comprise various combinations of implant assemblies, components and insertion instruments. A kit may comprise, for example, various combinations of fibrous implants, coiled bodies, coiled sleeve, insertion devices, other implants, and/or a cannula or other introducer. Optionally, a kit may include, for example, a syringe or other container of a cement or other bone filler material. A kit may also optionally include an external fixation apparatus or other tool for repositioning or fixing vertebrae or other bones or body segments. One skilled in the art will appreciate that various other combinations of devices, components and assemblies can be made and are intended to fall within the scope of the present invention.

In another embodiment, the vertebral body implant may comprise a coiled sleeve. Referring to FIG. 45A, a coiled body 3300, also referred to herein as coil 3300 or body 3300, comprises one or more sheets 3312 coiled about a central axis 3316. Body 3300 may be approximately cylindrical, and can have an inner surface 3302, an outer surface 3304, and a diameter 3310, which may have an initial value of d1. Body 3300 can be dimensioned to fit within any desired cavity or space. For example, in some embodiments, coiled body 3300 can be dimensioned to fit within a collapsed vertebral body. Diameter d1 3310 may be less than a diameter of a cannula or other device having a lumen through which coil 3300 can be passed. After insertion of coiled body 3300 into a collapsed vertebral body, a bone cavity, an intervertebral space, or another location, body 3300 can be partially uncoiled as shown in FIG. 45B. Such uncoiling can cause a widening of spaces 3314 between coils of sheet 3312, and a concomitant increase in diameter 3310 from d1 to d2. Such coiling may alternatively and/or additionally cause an increase in the diameter of the coiled body. Uncoiling of body 3300 may be performed, for example, by rotation of body 3300 with respect to axis 3316, e.g., in a direction opposite the direction of coiling of sheet 3312 about axis 3316.

Sheet 3312 can comprise one or more metals, composite materials, polymers, or the like, and preferably has a stiffness and an outward bias when coiled. Such outward bias can be sufficient to provide a desired radial force when body 3300 is partially uncoiled as shown in FIG. 45B. In some embodiments, coiled sheet 312 can comprise stainless steel, aluminum, a metal alloy, e.g., a cobalt alloy, a nickel titanium alloy or another alloy, a polymer, or any combination thereof. Body 3300 can be radiopaque or non-radiopaque. In certain embodiments, sheet 3312 can comprise a nickel titanium alloy having shape memory characteristics.

Referring to FIGS. 46A and B, an augmentation device 5400 comprises coiled body 5300 coiled around an axial member, or shaft 5410. As shown in FIG. 46A, a minimally invasive method of augmenting a damaged vertebral body, e.g., following a vertebral compression fracture, comprises inserting a augmentation device 5400 into a portion 5402, preferably central portion 5402, of vertebral body 12, for example through a cannula or other introducer (not shown). Suitable procedures and materials for inserting a cannula through which coil 5300 may be introduced are known in the art, and may be similar to those described above for kyphoplasty and other procedures. For example, device 5400 may be introduced through the posterior portion 20 of the vertebral body 12, e.g., through pedicle 24 (e.g., transpedicular approach).

After coil 5300 is inserted into central portion 5402 of vertebral body 12, shaft 5410 may be rotated to partially uncoil body 5300. Uncoiling body 5300 can increase its diameter 5310, for example from d1 to d2 as shown in FIG. 46B. As diameter 5310 of coil 5300 increases, surface 5304 of coil 5300 can impart a radial force against endplates 5402, 5404 of vertebral body 12. Such radial force can push endplates 5406, 5408 apart, which can restore vertebral body 12 to its original height and augment or stabilize the vertebral body 12. Additionally, the radial force imparted by expanding coil 5300 can compact the bone inside vertebral body 12, which may aid in integration of the device 5400 within cavity 5402 of vertebral body 12.

Figure 47:
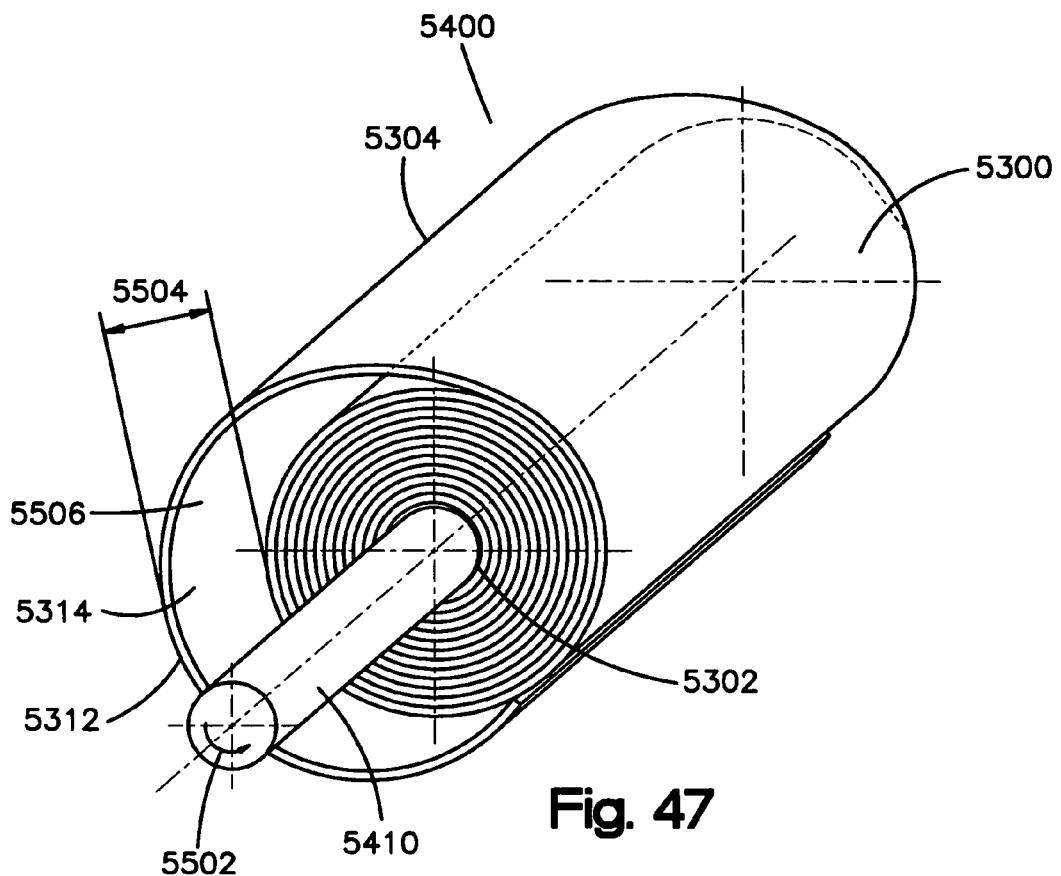
FIG. 47 is a perspective view illustration of an expandable augmentation device according to an embodiment of the present invention.

FIG. 47 illustrates a close-up perspective view of an augmentation device 5400 according to an embodiment of the present invention. Expandable body 5300 can comprise a rigid or semi-rigid sheet 5312, which can be tightly coiled around axial member, or shaft, 5410 as shown. Axial member 5410 can, for example, be a solid member or can have a lumen through which objects may be passed. In some embodiments, sheet 5312 is attached to shaft, for example at inner surface 5302 of coil 5300. Body 5300 can be expanded by partially uncoiling sheet 5312, which can create or increase spaces 5314 between layers of sheet 5312, and/or increase the space in the center of the body 5300. Such uncoiling can be performed, for example, by rotating axial member 5400. In one embodiment, body is expanded by rotating axial member 5410 in a direction 5502 opposite the direction of coiling of sheet 5312, which can result in an outward displacement 5504 of one or more outer coils 5506 of sheet 5312.

In other embodiments, body 5300 can be held in a tightly coiled position within the lumen of a cannula or other sheath, and such sheath may be removed from coil 5300 after implantation within a bone 12. In such embodiments, sheet 5312 may be uncoiled by rotation of shaft 5502 as described above, or sheet 5312 may have sufficient stiffness, rigidity or memory that upon removal of the sheath the sheet 5312 partially uncoils within bone 12, e.g., with sufficient force to impart a desired radial force to augment the bone 12.

In some embodiments, coil 5300 and axial member 5410, or a portion of axial member 5410, can remain in vertebral body. In other embodiments, coil 5300 can remain in vertebral body 12 after the axial member 5410 is removed from the patient, e.g. along with a cannula, sheath, or other introducer. Keeping coil 5300 in vertebral body 12 can, for example, help continue augmenting the vertebra and maintain proper lordosis. In other embodiments, PMMA or another cement or filler can be inserted into vertebral body 12, e.g., through shaft and/or a cannula, along with coil 5300 to further enhance fixation or repair of the damaged region. In other embodiments, coil 5300 and/or shaft 5410 can be removed after repositioning the bone, and PMMA or another filler can be injected into a void created by coil 5300.

In other embodiments, body 5300 can include multiple sheets 5312 and/or can include an expandable bag, balloon, or other device between one or more coils of sheet 5312 and/or within lumen 5316 to facilitate expansion of body 5300 within vertebral body 12.

Figure 48:
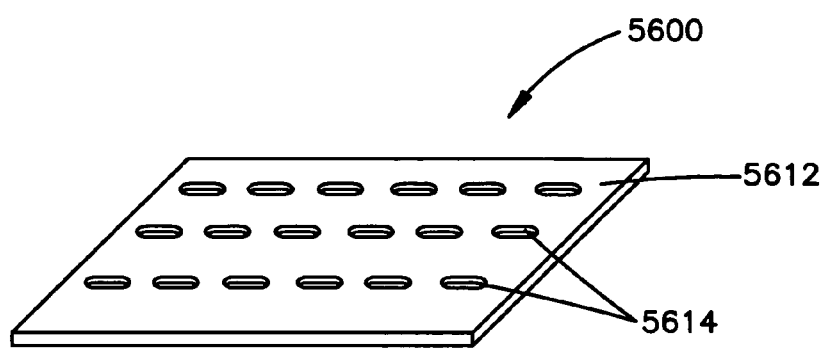
FIG. 48 is a perspective view schematic illustration of a fenestrated sheet for use in an augmentation device according to the present invention.

FIG. 48 is a perspective view schematic illustration of a fenestrated sheet 5600 for use in an expandable augmentation device according to the present invention. In some embodiments sheet 5600 may comprise a rigid or semi-rigid material 5612 that can be formed into a coil. Suitable materials may include, for example, stainless steel, aluminum, a metal alloy, e.g., a cobalt alloy, a nickel titanium alloy or another alloy, a polymer, or any combination thereof. Sheet 5600 can include a plurality of holes 5614, for example through which a cement or other filler material may pass.

Figure 49:
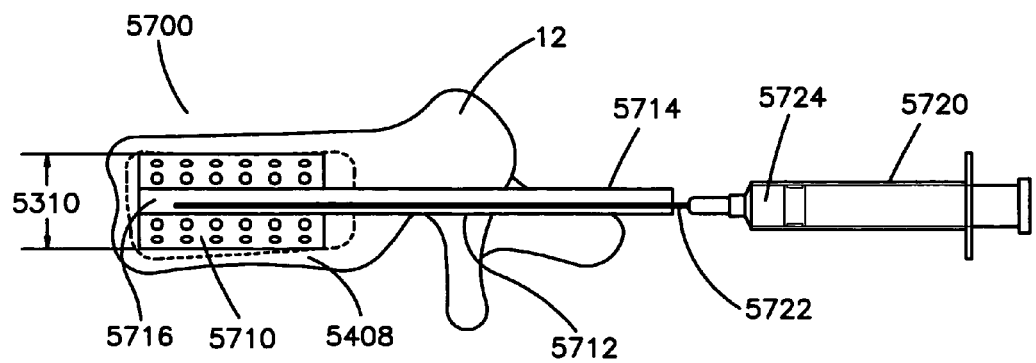
FIG. 49 is a cross-sectional side view of an embodiment of an augmentation device having a coiled fenestrated sheet in use within a vertebral body.

Referring to FIG. 49, an augmentation device 5700 may comprise a coil 5710 of fenestrated sheet material 5612, which may include holes 5614, coiled around an end 5716 of an axial member 5712. Axial member 5712 can include a lumen 5714, through which a needle 5722 or other device or material may be passed. End 5716 of axial member 5712 may be open and/or axial member 5712 may include side holes near end 5716 to allow material within lumen 5714 to pass into body 5710.

In use, coil 5710 can be inserted into a central portion 5402 of a vertebral body 12, e.g., using a transpedicular approach. Body 5710 may be uncoiled to a desired diameter 5310, e.g., to impart a radial force on endplates 5406, 5408 and restore anterior portion of vertebral body 12 to its original height. Such uncoiling of body 5710 may be performed, for example, by rotating axial member 5712 in a direction opposite of the direction of coiling of sheet material 5612. The filler material can uncoil or otherwise expand, or assist in the expansion of body 5710 in combination with other expansion means. In other embodiments, body 5710 uncoils without rotating shaft, e.g., due to the stiffness or rigidity of material 5612. A needle 5722 or other extension can pass through lumen 5714 toward end 5716 of axial member 5712 to inject or otherwise transfer bone cement or other filler material into coiled body 5710 from a syringe or other injection apparatus 5720. In other embodiments, injection apparatus 5720 can be coupled with an exposed end 5718 of axial member 5712. The injected bone cement or other filler material 5724 can flow from end 5716 of axial member, and through holes 5614 in fenestrated sheet material 5612, e.g., to surround coils of body 5710 and preferably aid in augmenting vertebral body 12. In some embodiments, after injection of filler material 5724, axial member 5712 can removed, leaving coiled body 5710 and filler material 5724 inside vertebral body 12. In other embodiments, axial member 5712 is not detached from body 5710. The coiled body 5710 can be releasably attached to the axial member 5712.

Figures 50A, 50B:
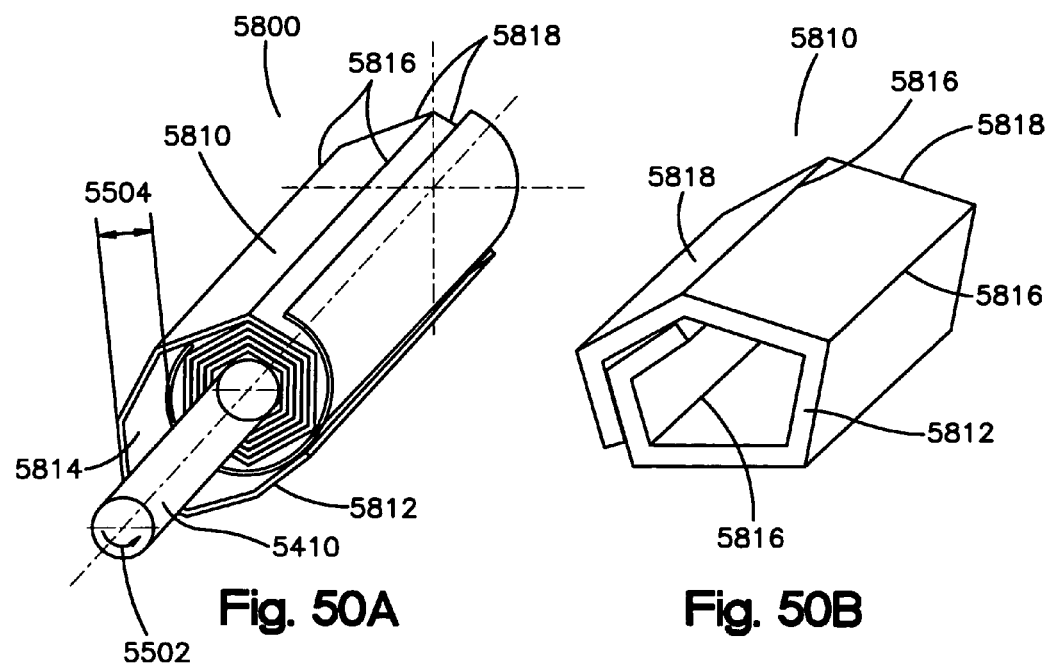
FIGS. 50A and B are perspective views of another embodiment of an augmentation device according to the present invention.

Referring to FIGS. 50A and B, an augmentation device 5800 according to another embodiment of the invention comprises a coiled body 5810 comprising one or more sheets 5812 coiled around an axial member 5410. As described above with respect to augmentation devices 5400 and 5700, sheet 5812 can comprise materials having any desired dimensions, strength, rigidity, stiffness, elasticity, thickness, flexibility or other characteristics. In some embodiments, sheet 5812 comprises stainless steel, aluminum, a metal alloy, e.g., a cobalt alloy, a nickel titanium alloy or another alloy, a polymer, or any combination thereof. Sheet 5812 can further comprise perforations, hinge features or other joints 5816 between adjacent panels or segments 5818 of sheet 5812. Such joints can facilitate coiling (collapse) and/or uncoiling (expansion) of sheet 5812 and allow for use of substantially rigid sheet material 5812.

In use, axial member 5410 can be rotated, for example in a direction 5502 opposite the direction of coiling of sheet 5812 around axial member. Such rotation can cause uncoiling or expansion of sheet 5812, increasing or creating space 5814 between coils and causing an outward expansion 5504 of body 5810. Thus, the coiled body can be implanted in a first size and thereafter to a second size inside the vertebral body. Joints 5816 provide discrete locations for the sheet to bend or pivot, e.g., between segments 5818. Joints 5816 can thus provide for incremental increases in diameter of coiled body 5810. By having joints 5816, substantially rigid materials can be employed in segments 5818 of sheet 5812, which may help optimize outward, radial forces imparted by body 5810 as it is expanded within a bone or other confined area such as within a vertebral body.

Figure 51:
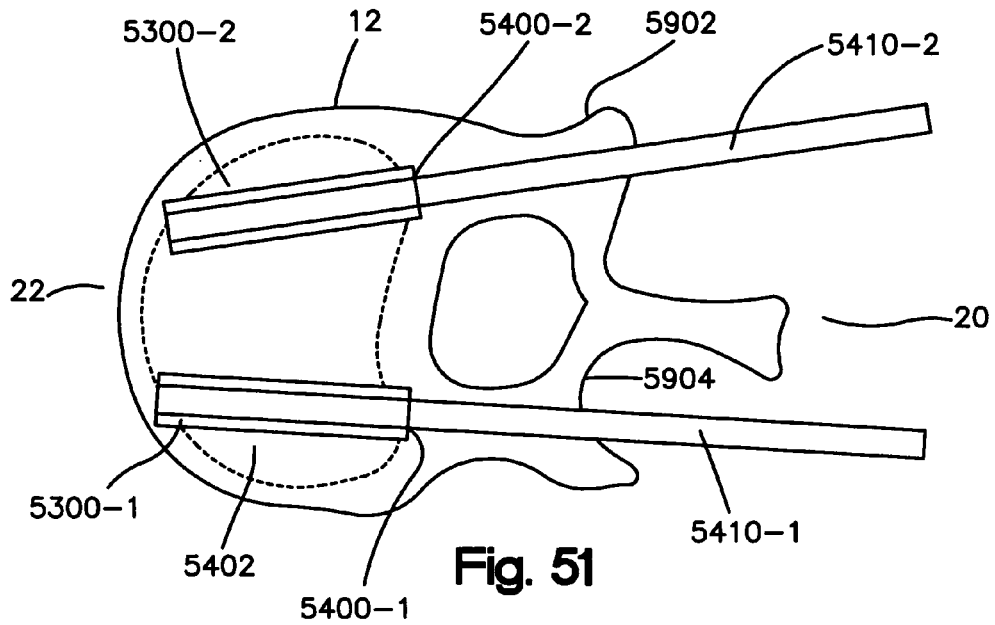
FIG. 51 is a cross-sectional top view illustration of another embodiment of an apparatus and method according to the present invention.

Referring to FIG. 51, a method of augmenting a vertebral body or other bone can comprise inserting multiple augmentation devices 5400-1 and 5400-2 into a vertebral body 12, e.g., using a posterior 20 transpedicular approach, e.g. through pedicles 5902, 5904. In one embodiment, augmentation devices 5400-1 can include a body 5300-1 coiled about an axial member 5410-1, and can be inserted into a central portion 5402 of a vertebral body 12, e.g., adjacent to a pedicle 5902. A second augmentation device, for example 5400-2 which can also include a body 5300-2 coiled about an axial member 5410-2, 2 or wool bales, or coiled bobbin can also be inserted into central portion 5402, e.g., through an opening adjacent to opposite pedicle 904. One or both of devices 5400-1 and 5400-2 can have some or all of the features described above with respect to augmentation devices 5400, 5700 and/or 5800, e.g., rigid or semi-rigid materials, fenestrated sheets, joints, and/or various other features described herein. After insertion of devices 5400-1 and 5400-2, one or both bodies 5300-1 and 5300-2 can be uncoiled or otherwise expanded as described above to increase the height of vertebral body 12. Devices 5400-1 and 5400-2 can then be removed, or some or all of one or both devices 5400-1 and 5400-2 (e.g., bodies 5300-1 and 5300-2) can remain to augment vertebral body. In some embodiments, a bone cement or other filler material can be inserted into space 5402, with or without coiled bodies 5300-1 and 5300-2 remaining in the vertebral body, to facilitate augmentation. The bone cement or other filler material may alternatively, or additionally, be inserted into the vertebrae so that it plugs the opening into the vertebrae to prevent expulsion of the implant.

Figures 52A, 52B:
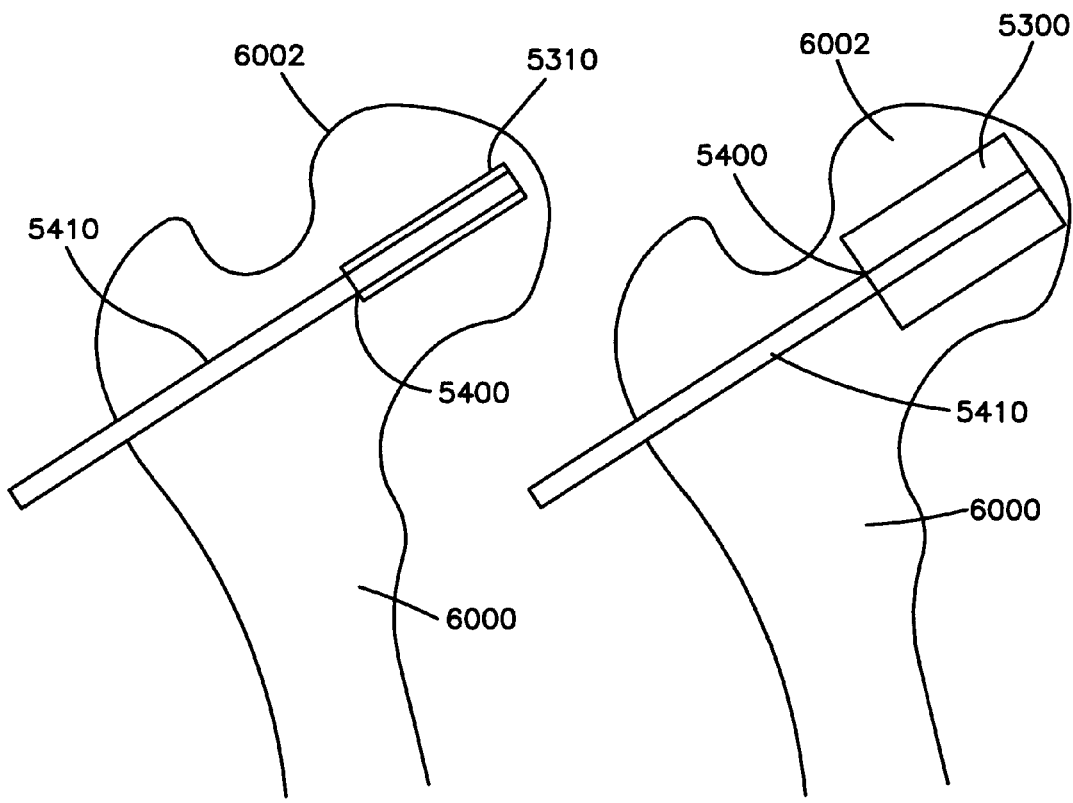
FIGS. 52A and B are cross sectional views of an expandable osteopathic augmentation device in use in a proximal femur according to an embodiment of the present invention.

Although the apparatus and methods described herein thus far have been described in the context of repositioning and augmenting vertebral bodies following vertebral compression fractures, various other uses and methods are envisioned. For example, in some embodiments, an expandable device 5400 comprising, for example a coiled sheet 5300, may be used to reposition and/or augment other damaged bone regions such as a fractured or weak proximal femur 6000 as shown in FIGS. 52A and B. In such embodiments, device 5400 may be inserted into a head 6002 of femur 6000, e.g., through a cannula or other introducer. Once inserted, coiled body 5300 of device 5400 can be partially uncoiled to expand the diameter of body 5300 as shown in FIG. 52B, and to provide a radial force to reposition and/or augment damaged head 6002. Such uncoiling can be performed, for example, by rotating axial member 5410 as described above, or by removing a restraining sheath or other device from coiled body. A bone cement or other filler can also be used to aid augmentation, or plug the insertion bore in the bone.

In some embodiments, the implants and methods described herein can be used in conjunction with other apparatus and methods to restore lordosis and augment vertebral body. For example, one or more augmentation devices 5400, 5700, 5800 may be used in conjunction with known procedures, e.g., a balloon kyphoplasty, that can be used to begin repositioning of a vertebral body and/or create a space within the body for device 5400, 5700 or 5800. In other embodiments, augmentation devices 5400, 5700, 5800 may be used in conjunction with an external fixation device that attaches to one or more vertebral bodies to aid in repositioning the vertebral the vertebral bodies before or after insertion of the devices 5400, 5700, 5800. In other embodiments, one or more axial members, e.g. members 5410 or 5712, can be manipulated by a user or attached to a fixation frame or other apparatus to facilitate repositioning of vertebral bodies.

In another embodiment, a kit comprises various combinations of assemblies and components according to the present invention. A kit may include, for example, a cannula and one or more wool bales, coiled bodies, coiled bobbins according to the present invention. The one or more wool bales, coiled bodies, coiled bobbins may be provided in different sizes, e.g., different lengths and/or diameters (widths). In other embodiments, a kit may include a cannula and/or sheath, one or more wool bales, coiled bodies, coiled bobbins, and a syringe or other apparatus for injecting a cement or other filler into a vertebral body. One skilled in the art will appreciate that various other combinations of devices, components and assemblies can be made and are intended to fall within the scope of the present invention.

In other embodiments, various minimally invasive implants and methods for alleviating discomfort associated with the spinal column may employ an augmentation device, such as wool bales, coiled bodies, coiled bobbins, having one or more of the features described herein. For example, coiled sheet with or without an axial member can be implanted between spinous processes of adjacent vertebrae to distract the processes and alleviate pain and other problems caused for example by spinal stenosis, facet arthropathy, and the like. For example, augmentation systems described herein may be used instead of or in addition to expandable interspinous process apparatus and methods described in U.S. patent Publication No. 2004/018128 and U.S. Pat. No. 6,419,676 to Zucherman et al.

The augmentation devices/systems described herein may be used for other purposes other than the femur and vertebrae.

While the foregoing description and drawings represent the preferred embodiments of the present invention, it will be understood that various additions, modifications and substitutions may be made therein without departing from the spirit and scope of the present invention as defined in the accompanying claims. In particular, it will be clear to those skilled in the art that the present invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components and otherwise, used in the practice of the invention, which are particularly adapted to specific environments and operative requirements without departing from the principles of the present invention. In addition, the features described herein can be used singularly or in combination with other features. The presently disclosed embodiments are therefore to be considered in all respects as illustrative and not restrictive, the scope of the invention being indicated by the appended claims, and not limited to the foregoing description.

What is claimed is:

1. A bone treatment system comprising:
a bobbin having a longitudinal axis along which the bobbin is insertable into an interior cavity of a bone, a diameter transverse to the longitudinal axis, a first end and a second end, the bobbin configured for implantation within a bone;
a band having a length substantially larger than its width or height, the band configured to contact and coil multiple times around the bobbin between the first and second ends to increase the diameter of the bobbin when the bobbin is implanted within bone, and
a guide mechanism having a longitudinal axis along which the guide mechanism is insertable into the interior cavity of the bone, the longitudinal axis of the guide mechanism being parallel to the longitudinal axis of the bobbin so that the bobbin and the guide mechanism are insertable through a single incision, the guide mechanism being axially moveable with respect to the bobbin along the longitudinal axis of the bobbin between the first and second ends and controlling a position of the band between the first and second ends of the bobbin while the band is being coiled around the bobbin, the band is coiled between the bobbin and the guide mechanism such that the guide mechanism limits the diameter of the band about the bobbin, wherein coiling of the band about the bobbin can be performed manually or with the aid of a mechanized tool.

2. The system of claim 1 further comprising:
an elongated body having a longitudinal axis, a proximal end and a distal end, the proximal end configured for manipulation by a user outside the patient to place the distal end in a desired position within the bone, the longitudinal axis of the elongated body being parallel to the longitudinal axis of the bobbin; and
a joint disposed between the second end of the bobbin and the distal end of the elongated body.

3. The system of claim 2, wherein the bobbin is cylindrical and comprises a hole through which a portion of said band passes.

4. The system of claim 2,
wherein the elongated body comprises at least a portion of a drive line assembly to rotate the bobbin, the elongated body is configured to rotate, and the joint is configured to transfer rotation from the elongated body to rotate the bobbin, and
wherein the joint is releasable so that the elongated body can be detracted from the bobbin.

5. The system of claim 1, further comprising:
a drive line assembly configured to releasably attach to and to rotate the bobbin and having a proximal end and a distal end, the proximal end configured in use to extend from the patient and be manipulated by a user to place the distal end in a desired position in the bone, the distal end releasably connected to the bobbin.

6. The system of claim 5, wherein the drive line assembly comprises a rotatable shaft and the guide mechanism comprises an elongated tube coaxial with the rotatable shaft, the elongated tube moveable in an axial direction relative to the bobbin and contacting the band to position the band between the first and second ends of the bobbin.

7. The system of claim 6, further comprising a knob connected to the elongated tube and containing a guide hole for the band.

8. The system of claim 6, wherein the bobbin has threads to assist in guiding the band.

9. The system of claim 5, wherein the drive line assembly comprises a rotatable shaft, the shaft capable of transferring torque to the bobbin, and
wherein the guide mechanism comprises a guide tube having a proximal end and a distal end through which the band moves, the guide tube movable axially with respect to the shaft.

10. The system of claim 9, wherein the rotatable shaft and guide tube are located in a needle, the rotatable shaft is axially fixed with respect to the needle and the guide tube moves axially with respect to the needle, wherein a portion of the needle is positioned along side and adjacent the bobbin.

11. The system of claim 9, wherein the drive line assembly includes a gear and a rotatable cam disk to convert the rotary motion of the drive line assembly to an axial motion, the gear and the rotatable cam disk connectable to the drive line assembly and the guide tube to move the guide tube axially.

12. The system of claim 11, wherein the gear is connectable with the drive line assembly, the rotatable cam disk and an axially moveable but non-rotatable follower, the cam disk having a groove along its outer surface and the follower including a projection, the projection extending into the groove.

13. The system of claim 12, wherein the follower is a spool holder and the projection is a dowel pin insertable through a hole in the spool holder.

14. The system of claim 1, wherein the band is coated with or form part of a matrix with other materials to include osteo-inductive materials, osteo-conductive materials, antibiotics, tricalcium phosphate, bone morphogenetic proteins.

15. The system of claim 1, wherein the band, having radio opaque properties, is resistant to tension of at least 100 N, and wherein the band slides along the tissue of the bone but not along the outer diameter of the bobbin.

16. The system of claim 1, wherein the band may be composed of suture material, metal, metal coated with bone material, metal with a polymer surface allowing for welding the bobbin and surrounding tissue together.

17. The system of claim 1, further comprising:
an insertion device sized and configured to insert the bobbin within a bone, the insertion device configured to cause the band to coil multiple times around the bobbin between the first and second ends to increase the diameter of the bobbin and band assembly, the insertion device releasably connectable to the bobbin,
wherein the insertion device comprises a drive line assembly to apply a rotational force to the bobbin to cause the bobbin to rotate about its longitudinal axis to coil the band around the bobbin, to increase the diameter of the bobbin and band assembly.

18. The of claim 17, wherein: the drive line assembly comprises a rod connected to the bobbin, the rod being rotatable which in turn rotates the bobbin, wherein the guide mechanism comprises an outer cannula, causing the band to reposition along the length of the bobbin; and wherein continued rotation of the bobbin causes the diameter of the bobbin and band assembly to increase due to the coiling of the band around the bobbin.

19. A bone treatment system:
- a bobbin having a longitudinal axis, a diameter, a first end and a second end, the bobbin configured for implantation within a bone;
- a band having a length substantially larger than its width or height, the band configured to contact and coil multiple times around the bobbin between the first and second ends to increase the diameter of the bobbin when the bobbin is implanted within bone;
- a guide mechanism having a longitudinal axis parallel to the longitudinal axis of the bobbin, the guide mechanism being axially moveable with respect to the bobbin along the longitudinal axis of the bobbin, the guide mechanism controlling a position of the band between the first and second ends of the bobbin while the band is being coiled around the bobbin, the band is coiled between the bobbin and the guide mechanism such that the guide mechanism limits the diameter of the band about the bobbin,
- wherein coiling of the band about the bobbin can be performed manually or with the aid of a mechanized tool;
- an insertion device sized and configured to insert the bobbin within a bone, the insertion device configured to cause the band to coil multiple times around the bobbin between the first and second ends to increase the diameter of the bobbin and band assembly, the insertion device releasably connectable to the bobbin,
- wherein the insertion device comprises a drive line assembly to apply a rotational force to the bobbin to cause the bobbin to rotate about its longitudinal axis to coil the band around the bobbin, to increase the diameter of the bobbin and band assembly, the drive line assembly comprises a drive mechanism, a drive shaft, and a flexible shaft connected serially to the bobbin; the guide mechanism comprising a band guide conduit, a spool holder, and a rotatable cam disk; wherein the cam disk and spool holder converts the rotational force of the cam disk to an oscillating force applied to the band guide conduit causing the band guide conduit to move forward and backward relative to the bobbin; and wherein the band guide conduit comprises an interior passage way having a proximal and distal opening and wherein the band is positioned in and moves through the interior passage way of the band guide conduit out the distal opening where it coils around the bobbin.

20. The system of claim 17, wherein the insertion device further comprises a drive gear, a sprocket, and another gear to couple the drive shaft of the drive line assembly to a cam disk on the guide mechanism so as to have the cam disk rotates at a different velocity than the drive shaft.

21. A bone treatment system comprising:
- a bobbin having a longitudinal axis, a diameter, a first end and a second end, the bobbin configured for implantation within a bone;
- a band having a length substantially larger than its width or height, the band configured to contact and coil multiple times around the bobbin between the first and second ends to increase the diameter of the bobbin when the bobbin is implanted within bone, and
- a guide mechanism having a longitudinal axis parallel to the longitudinal axis of the bobbin, the guide mechanism being axially moveable with respect to the bobbin along the longitudinal axis of the bobbin, the guide mechanism controlling a position of the band between the first and second ends of the bobbin while the band is being coiled around the bobbin, the band is coiled between the bobbin and the guide mechanism such that the guide mechanism limits the diameter of the band about the bobbin,
- wherein coiling of the band about the bobbin can be performed manually or with the aid of a mechanized tool, and
- an insertion device sized and configured to insert the bobbin within a bone, the insertion device configured to cause the band to coil multiple times around the bobbin between the first and second ends to increase the diameter of the bobbin and band assembly, the insertion device releasably connectable to the bobbin,
- wherein the insertion device comprises:
  - a drive line assembly to apply a rotational force to the bobbin to cause the bobbin to rotate about its longitudinal axis to coil the band around the bobbin, to increase the diameter of the bobbin and band assembly, the drive line assembly comprises a drive mechanism, a drive shaft and a flexible shaft connected serially to the first end of the bobbin;
  - the guide mechanism comprising a band guide conduit, a spool holder, and a rotatable cam disk, wherein the cam disk having a groove along its outer surface and the spool holder including a projection, the projection extending into the groove of the cam disk; and
  - a drive gear, a sprocket, and another gear for coupling the drive shaft of the drive line assembly to the cam disk of the guide mechanism so as to have the cam disk rotate at a different velocity than the drive shaft,
- wherein the cam disk and spool holder converts the rotational force of the cam disk to an oscillating force applied to the band guide conduit causing the band guide conduit to move forward and backward relative to the bobbin, and
- wherein the band guide conduit comprises an interior passage way having a proximal and distal opening and wherein the band is positioned in and moves through the interior passage way of the band guide conduit out the distal opening where it coils around the bobbin,
- wherein the flexible shaft and band guide conduit are located in a needle, the flexible shaft is axially fixed with respect to the needle and the band guide conduit moves axially with respect to the needle,
- wherein a portion of the needle is positioned along side and adjacent the bobbin, and
- wherein continued rotation of the bobbin causes the diameter of the bobbin and band assembly to increase due to the coiling of the band around the bobbin.

* * * * *